US008201752B2

(12) United States Patent
Brodbeck et al.

(10) Patent No.: US 8,201,752 B2

(45) Date of Patent: Jun. 19, 2012

(54) LOW ENERGY VAPORIZATION OF LIQUIDS: APPARATUS AND METHODS

(75) Inventors: Kelly James Brodbeck, Danville, CA (US); Warren Saul Breslau, Berkeley, CA (US); Erick Mathew Davidson, El Cerrito, CA (US); Gregory van Buskirk, Danville, CA (US)

(73) Assignee: Vapore, Inc., Concord, CA (US)

( * ) Notice: Subject to any disclaimer, the term of this patent is extended or adjusted under 35 U.S.C. 154(b) by 298 days.

(21) Appl. No.: 12/388,519

(22) Filed: Feb. 19, 2009

(65) Prior Publication Data

US 2009/0224064 A1 Sep. 10, 2009

Related U.S. Application Data

(60) Provisional application No. 61/068,727, filed on Mar. 10, 2008.

(51) Int. Cl.
*B05B 1/24* (2006.01)

(52) U.S. Cl. ........................................... 239/13; 239/45

(58) Field of Classification Search .................... 239/13, 239/136, 128, 139, 133, 338, 41–44, 53
See application file for complete search history.

(56) References Cited

U.S. PATENT DOCUMENTS

| | | | |
|---|---|---|---|
| 799,581 | A | 9/1905 | Trewhella |
| 1,225,381 | A | 5/1917 | Wedge et al. |
| 1,944,821 | A | 12/1931 | Blaise et al. |
| 1,905,610 | A | 4/1933 | Stoll |
| 3,234,928 | A | 2/1966 | Smith |
| 3,262,290 | A | 7/1966 | Huber |
| 3,542,247 | A | 11/1970 | Racek |
| 3,663,152 | A | 5/1972 | Yoshida |
| 3,781,518 | A | 12/1973 | Power |
| 3,820,540 | A | 6/1974 | Hirtz |
| 3,869,242 | A | 3/1975 | Schladitz |
| 4,134,718 | A | 1/1979 | Kayfetz et al. |
| 4,193,755 | A | 3/1980 | Guarnaschelli et al. |
| 4,207,055 | A | 6/1980 | Tanaka |

(Continued)

FOREIGN PATENT DOCUMENTS

JP 04024490 A 1/1992

OTHER PUBLICATIONS

Vapore CFV Technology web site pages: http://vapore.com (Aug. 23, 2011).

(Continued)

*Primary Examiner* — Davis Hwu

(74) *Attorney, Agent, or Firm* — The Firenza Group Ltd.; Sharon R. Kantor

(57) ABSTRACT

The present invention relates to an apparatus and method for the low energy flash-like vaporization of liquids and the release of the resulting vaporized liquid into the atmosphere in the form of a visible plume, mist or cloud. Vaporization is occasioned in a geometrically small device capable of producing vaporized liquid that varies little in composition in comparison to the starting liquid feed to the device. The apparatus and method are primarily directed towards the treatment of small areas for residential air fragrancing, odor elimination, treatment of insects or pests, air sanitization, air and surface antibacterial or antimicrobial treatment, administration of personal pharmaceuticals or medicaments, as well as other ambient air or surface modification by way of gas, vapor or droplet distribution.

20 Claims, 4 Drawing Sheets

U.S. PATENT DOCUMENTS

| | | | |
|---|---|---|---|
| 4,318,689 A | 3/1982 | Förster | |
| 4,325,345 A | 4/1982 | Wilkinson et al. | |
| 4,365,952 A | 12/1982 | Ohmukai et al. | |
| 4,465,458 A | 8/1984 | Nishino et al. | |
| 4,532,088 A | 7/1985 | Miller | |
| 4,552,124 A | 11/1985 | Nakajima | |
| 4,571,481 A | 2/1986 | Leary | |
| 4,635,630 A | 1/1987 | Noir et al. | |
| 4,657,713 A | 4/1987 | Miller | |
| 4,684,341 A | 8/1987 | Kawamura et al. | |
| 4,703,888 A | 11/1987 | Kawamura et al. | |
| 4,857,421 A | 8/1989 | Ernst | |
| 4,909,999 A | 3/1990 | Cummings et al. | |
| 5,039,351 A | 8/1991 | Cooper et al. | |
| 5,113,478 A | 5/1992 | Nakashima et al. | |
| 5,178,210 A | 1/1993 | Guillet et al. | |
| 5,179,966 A | 1/1993 | Losee et al. | |
| 5,224,498 A | 7/1993 | Deevi | |
| 5,228,922 A | 7/1993 | Sievers | |
| 5,338,383 A | 8/1994 | Polackowyj | |
| 5,484,086 A | 1/1996 | Pu | |
| 5,692,095 A | 11/1997 | Young | |
| 5,743,251 A | 4/1998 | Howell et al. | |
| 5,870,525 A | 2/1999 | Young | |
| 5,928,436 A | 7/1999 | Borkowski et al. | |
| 5,938,693 A | 8/1999 | Carminucci | |
| 5,939,666 A | 8/1999 | Sievers et al. | |
| 5,940,577 A | 8/1999 | Steinel | |
| 5,998,728 A | 12/1999 | Sievers et al. | |
| 6,102,037 A | 8/2000 | Koch | |
| 6,104,867 A | 8/2000 | Stathakis et al. | |
| 6,162,046 A | 12/2000 | Young et al. | |
| 6,169,852 B1 | 1/2001 | Liao et al. | |
| 6,234,167 B1 | 5/2001 | Cox et al. | |
| 6,236,807 B1 | 5/2001 | Ruffolo et al. | |
| 6,263,872 B1 * | 7/2001 | Schuster et al. | 128/203.26 |
| 6,269,221 B1 | 7/2001 | Horie et al. | |
| 6,347,936 B1 | 2/2002 | Young et al. | |
| 6,431,167 B1 * | 8/2002 | Gonda et al. | 128/200.14 |
| 6,491,233 B2 | 12/2002 | Nichols | |
| 6,501,052 B2 | 12/2002 | Cox et al. | |
| 6,509,112 B1 | 1/2003 | Luft et al. | |
| 6,516,796 B1 | 2/2003 | Cox et al. | |
| 6,557,552 B1 | 5/2003 | Cox et al. | |
| 6,568,390 B2 | 5/2003 | Nichols et al. | |
| 6,585,509 B2 | 7/2003 | Young et al. | |
| 6,634,864 B1 | 10/2003 | Young et al. | |
| 6,681,769 B2 | 1/2004 | Sprinkel, Jr. et al. | |
| 6,681,998 B2 | 1/2004 | Sharpe et al. | |
| 6,701,921 B2 | 3/2004 | Sprinkel, Jr. et al. | |
| 6,701,922 B2 | 3/2004 | Hindle | |
| 6,715,487 B2 | 4/2004 | Nichols et al. | |
| 6,755,398 B1 | 6/2004 | Wong | |
| 6,766,220 B2 | 7/2004 | McRae et al. | |
| 6,772,757 B2 | 8/2004 | Sprinkel, Jr. | |
| 6,779,513 B2 | 8/2004 | Pellizzari et al. | |
| 6,799,572 B2 | 10/2004 | Nichols et al. | |
| 6,804,458 B2 | 10/2004 | Sherwood et al. | |
| 6,827,046 B2 | 12/2004 | Welle | |
| 6,854,461 B2 | 2/2005 | Nichols et al. | |
| 6,871,792 B2 | 3/2005 | Pellizzari | |
| 6,871,794 B2 * | 3/2005 | McEwen | 239/44 |
| 6,884,408 B2 | 4/2005 | Rabinowitz et al. | |
| 6,909,840 B2 | 6/2005 | Harwig et al. | |
| 6,923,179 B2 | 8/2005 | Gupta et al. | |
| 6,968,124 B1 | 11/2005 | Varanasi et al. | |
| 7,040,314 B2 * | 5/2006 | Nguyen et al. | 128/203.12 |
| 7,077,130 B2 | 7/2006 | Nichols et al. | |
| 7,169,378 B2 | 1/2007 | Rabinowitz et al. | |
| 7,175,934 B2 | 2/2007 | DeFilippis et al. | |
| 7,431,570 B2 | 10/2008 | Young et al. | |
| 7,540,286 B2 * | 6/2009 | Cross et al. | 128/204.17 |
| 7,920,777 B2 | 4/2011 | Rabin et al. | |
| 2004/0048000 A1 | 3/2004 | Shtein et al. | |
| 2004/0069242 A1 | 4/2004 | Welle | |
| 2006/0144395 A1 | 7/2006 | Koch et al. | |
| 2006/0196968 A1 | 9/2006 | Rabin et al. | |
| 2009/0224064 A1 | 9/2009 | Brodbeck et al. | |

OTHER PUBLICATIONS

Office Action dated May 2, 2002 with respect to U.S. Appl. No. 12/095,481.

Office Action dated Nov. 10, 2010 with respect to U.S. Appl. No. 12/108,484.

Office Action dated Sep. 15, 2010 with respect to U.S. Appl. No. 12/108,484.

Office Action dated Mar. 16, 2010 with respect to U.S. Appl. No. 12/108,484.

Office Action dated Jun. 25, 2010 with respect to U.S. Appl. No. 11/920,320.

Office Action dated Oct. 27, 2008 with respect to U.S. Appl. No. 11/355,461.

Int'l Preliminary Examination Report (IPER) dated Oct. 18, 2007 with respect to PCT/US2006/018696.

Office Action dated Oct. 17, 2006 with respect to U.S. Appl. No. 10/691,067.

Int'l Preliminary Examination Report (IPER) dated Aug. 9, 2008 with respect to PCT/US2006/046030.

Office Action dated Feb. 5, 2001 with respect to U.S. Appl. No. 10/079,636.

Office Action dated Feb. 5, 2001 with respect to U.S. Appl. No. 09/654,659.

Office Action dated Mar. 31, 2000 with respect to U.S. Appl. No. 08/899,181.

Office Action dated Dec. 8, 1999 with respect to U.S. Appl. No. 08/899,181.

Office Action dated Apr. 8, 1999 with respect to U.S. Appl. No. 08/899,181.

Office Action dated May 1, 1998 with respect to U.S. Appl. No. 08/946,033.

Office Action dated Dec. 4, 1996 with respect to U.S. Appl. No. 08/439,093.

Office Action dated Jul. 10, 1996 with respect to U.S. Appl. No. 08/439,093.

* cited by examiner

LOW ENERGY VAPORIZATION OF LIQUIDS: APPARATUS AND METHODS

BACKGROUND OF THE INVENTION

1. Field of the Invention

The present invention relates to an apparatus and method for the low energy flash-like vaporization of liquids. The resulting vaporized liquid is released into the atmosphere in the form of a condensation aerosol, giving rise to a visible plume, mist or cloud. The resulting plume, mist or cloud can rapidly dissipate. Vaporization is occasioned in a geometrically small device capable of producing vaporized liquid that varies little in composition in comparison to the starting liquid feed to the device. The apparatus and methods are primarily directed towards the treatment of small areas for residential air fragrancing, odor elimination, treatment of insects or pests, air sanitization, air and surface antibacterial or antimicrobial treatment, administration of personal pharmaceuticals or medicaments, as well as for other ambient air or surface modification by way of gas, vapor or droplet distribution.

2. Discussion of the Related Art

Traditional techniques for introducing liquids into the atmosphere for fragrancing or air treatment include such methods and devices such as potpourri, reed sticks, incense and warming stoves. Potpourri, which is dried, naturally fragrant plant material, is typically used to fragrance homes. With ambient air motion, fragrance wafts from the dried material to permeate room environments. Reed sticks are relatively new products in which fragranced compositions wick up a porous cellulosic shaft and are emitted into the room environment. Wood and bamboo are examples of often-used cellulosic shafts. Incense involves the use of aromatic, biologically derived materials. A fragrant smoke is released from the incense material upon burning, which is characteristically accompanied by smoke and soot. Warming stoves typically heat fragranced solids, oils or solutions by candles or other external means up to the smoke point to release fragrancing components into the ambient air. Again, such practice is often accompanied by smoke and soot.

More recent automatic techniques that are available for fragrancing or treating ambient air include devices such as: heated wick diffusers and products of the so-called "plug-in" variety; vibrating atomizers; and ultrasonic devices. Examples of heated wick and plug-in diffusers include: Glade® PlugIns®, sold by S.C. Johnson & Son, Inc., Racine, Wis.; Airwick® Scented Oil Warmers, sold by Reckitt Benckiser, Parsippany, N.J.; and Febreze® NOTICEables™, sold by Procter & Gamble, Cincinnati, Ohio; among others. An example of a vibrating atomization mesh or plate that employs a piezoelectric technique is the Glade® Wisp®, sold by S.C. Johnson & Son, Inc., Racine Wis. Essentially, this technique employs a vibrating element to shake liquid feed into the atmosphere. One problem associated with this technique is the poor mechanical reliability of the vibrating parts.

Aside from the device being prone to breakage during post-manufacture transport before reaching consumers, the mechanical elements appear to not be very robust and often break, shortly before or after use has commenced. The lack of robustness of the moving parts thus leads to average shorter product life for piezoelectric devices. Material can also build up on the vibrating element, leading to inefficient operation of the device. The latter results in greater energy being required to disperse the feed liquid and can result in poor fragrance dispersal or none whatsoever. An example of a pump atomizer is the Mr. Steam® Aromaflo® Oil Injector System available from Sussman-Automatic Corporation, Long Island City, N.Y. Examples of ultrasonic devices used for fragrancing air include: The Ultrasonic Fragrance Machine, from Stiers, GmbH of Aschheim, Germany; Ultrasonic Air Fragrance for Home or Car, sold by Ultronix Products Ltd., China; Ultrasonic Aromatherapy Essential Oil Atomizer, sold by Wedian Technology Co., Ltd., China; as well as the MABISMist™II Ultrasonic Nebulizer, an ultrasonic water vaporizer from MABIS® Healthcare.

Problems with several of the known techniques and devices mentioned above include: 1) difficulties with accurate control of the amount of material being vaporized or otherwise introduced into the air; 2) inability to view, sense, or perceive the liquid or other material as it is being vaporized; 3) reproducibility of droplet size, agglomeration of droplets, and like issues; and 4) habituation of scent over relatively short periods of time such as hours or days. Habituation as used herein is understood to pertain to a phenomenon in which an individual becomes sufficiently accustomed to a particular fragrance after a period of exposure such that the individual becomes unable to discern its presence; 5) the phenomenon of "rain out" over time, where the term rain out as used herein is understood to refer to the tendency for the deposition of aerosolized particles onto a surface; and 6) segmentation of the formula, which disrupts the so-called "scent fidelity" by the dispensing mechanism. Segmentation occurs especially with heated wick diffusers, whereby the composition of the vapor poorly matches the composition of the feed liquid. The vapor composition changes over time as lighter formula elements are vaporized initially and heavier formula components are vaporized thereafter.

Recently, in addition to the efficiency, delivery and aesthetics of fragrance and other actives, particular aspects of liquid dispersal devices have received even greater scrutiny. As increasing numbers of consumers have begun using these products, in particular the more recent automatic techniques, emerging issues have captured the attention of regulatory groups, such as: 1) energy utilization; 2) reliability of the device; 3) ability of the technique to faithfully convey to the atmosphere a composition as similar as possible to that of the original liquid, insecticide composition, fragrance, pharmaceutical preparation, medicament; and so forth; 4) the use of propellants and solvents for dispersal of vaporized liquid that are detrimental to the environment; and 5) the need for quiet and discrete operation. Each of the prior art methods described above exhibits one or more of the aforementioned shortcomings. A summary of the prior art liquid dispersal methods and associated disadvantages that have been discussed herein are summarized in Table 1:

TABLE 1

Summary of Perceived or Known Disadvantages of Competitive Technologies

| Competitive Technology | Perceived technology weakness |
|---|---|
| Heated Wick Diffusers | No visual signal to indicate that it is working.<br>Provides constant dose, causing rapid habituation such that the fragrance may not be perceived within hours or days.<br>Top notes evaporate out ahead of bottom notes, such that fragrance character changes over time, for example, over the course of a month.<br>Significant use of energy over lifetime of the device; about 1.5 to 2 kilowatt-hour per month.<br>The electrical heating element is constantly hot during use, which can potentially raise safety issues. |
| Scented Reed Diffusers | No visual signal to indicate that it is working<br>Poor transmission of fragrance<br>Intermittent manual attention required to periodically rotate the reeds.<br>Bottles can be tipped over and contents spilled; no secondary fragrance containment. |
| Fragrance oil warmers | Can emit soot and smoke that is reminiscent of incense<br>Relatively low fragrance impact, unless operated at temperatures that are unsafe to the touch. The oils that are typically used with such fragrance warmers are not very aromatic and the scent is highly localized.<br>Significant energy use, typically similar to or greater than the heated wick diffusers; about 1.5 to 2 kilowatt-hour per month.<br>Device must be periodically checked during operation for refilling and monitored for overheating. Consequently, potential danger if device permitted to go dry. |
| Propellant-Based Dispensers | Automated and manual aerosol cans that are used in institutional and industrial (I&I) settings are disadvantageous from environmental perspectives.<br>Formulations are typically comprised of environmentally harmful propellants.<br>Propellants and/or solvents in liquid formulations often result in emanation of unpleasant or undesirable scents.<br>Aerosol droplets can rain out, rapidly reducing fragrance impact. |
| Piezoelectric devices | Relatively short lifetime, due either to fouling from organic compounds, malfunction through poor manufacturing, or relatively short lifetime of vibrating components. |
| Pumped Atomizers and Nebulizers | Various devices are generally bulky and/or noisy.<br>Other devices tend to be messy in generating large quantities of condensation. |

As noted above, there are a number of disadvantages associated with prior art air treatment devices. It is therefore desired to provide devices for various kinds of air treatment that overcome these disadvantages. It is also desirable to require less constant monitoring and have minimal human intervention with air treatment devices, unlike current devices such as those that involve aerosol cans, candles, fragrance warmers, reed diffusers, and the like. Furthermore, certain devices that contain moving parts, such as piezoelectric devices or pumps are inherently given to breakdown through malfunction or innate lifetime. Finally, heated wick plug-in diffusers use significantly more energy to deliver desired doses of material over extended periods, due to highly inefficient heating of their wicking components to volatilize the organic compounds.

SUMMARY OF THE INVENTION

The present invention provides an apparatus and a method for the generation of pressurized vapor from a non-pressurized liquid feed that overcomes many of the disadvantages associated with the prior art devices used for air treatment discussed above. The inventive vaporizers described herein can be used in domestic, commercial, indoor, outdoor, fixed as well as portable applications. The apparatus includes a vaporizing device comprising a heater and a porous member matingly configured for heat transfer between the heater and the porous member. The apparatus may also include optional elements such as a fan, a wick, a housing as well as additional elements or combinations of any of the foregoing, depending upon the desired use or purpose for the vaporizing apparatus.

The vaporizers of the present invention are contemplated for use in pulsed energy applications. However, continuous use applications are also regarded as falling within the scope of the present invention. Surprisingly, the instant inventive vaporizers have demonstrated such energy efficiency and reliability that even in pulse-mode operation, the devices are capable of delivering greater quantities of vapor at lower power requirements per quantity of liquid vaporized than other prior art air treatment devices currently in use.

Thus, the present invention provides a vaporizer apparatus and methods for the low energy flash-like vaporization of liquids and the release of the resulting vaporized liquid into the atmosphere in the form of a visible plume, mist or cloud. Vaporization is occasioned in a geometrically small device capable of producing vaporized liquid that varies little in composition in comparison to the starting liquid feed to the device. The apparatus and method are primarily directed towards the treatment of smaller areas for residential air fragrancing, odor elimination, treatment of insects or pests, air sanitization, air and surface antibacterial or antimicrobial treatment, administration of personal pharmaceutical or medicament compositions, as well as other ambient air or surface modification by way of gas, vapor or droplet distribution.

Figure 6:
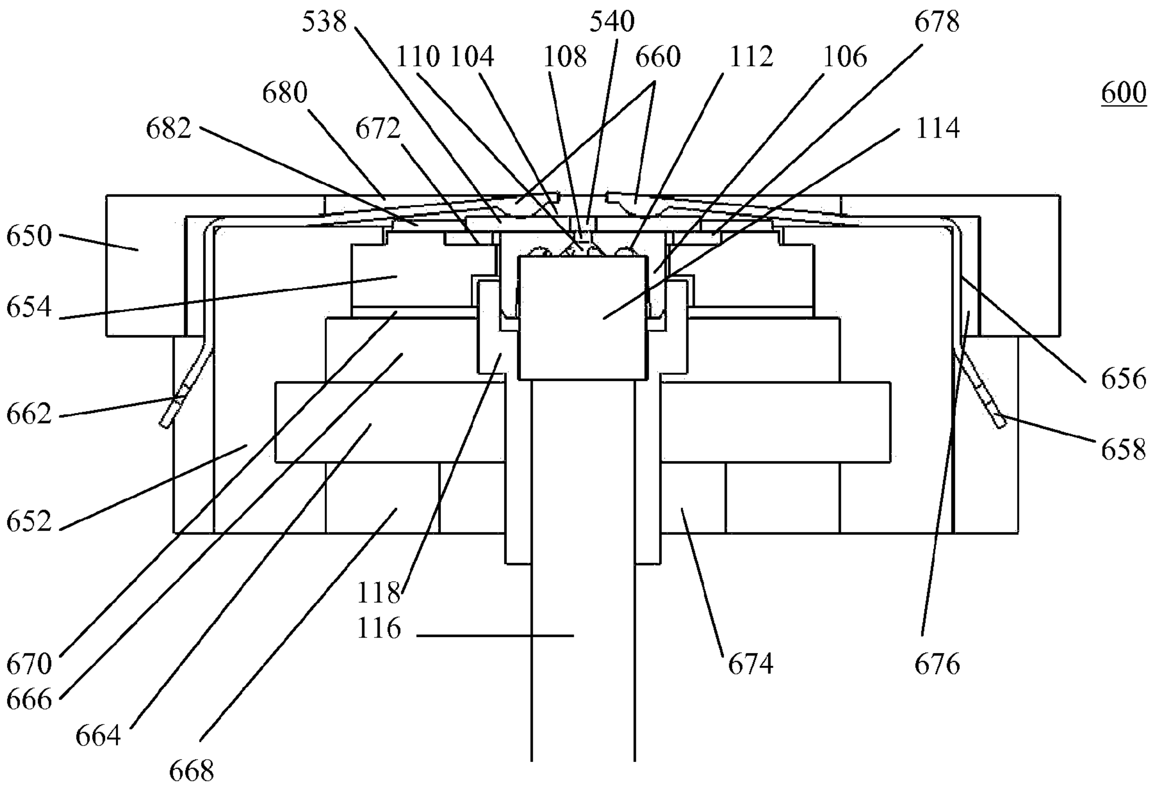
FIG. 6 is an illustration of a cross-section of a vaporizer according to still another embodiment of the present invention.

| Reference Numerals Used in the FIGURES: | |
|---|---|
| 100 | A first embodiment of a vaporization device of the present invention |
| 102 | Porous member cap |
| 104 | Heat trace |
| 106 | Side wall |
| 108 | Orifice |
| 110 | Fin, projection |
| 112 | Channel |
| 114 | Porous member |
| 116 | Optional wick |
| 118 | Housing |
| 200 | Second embodiment of a vaporization device of the present invention |
| 220 | First ledge |
| 222 | Second ledge |
| 224 | First gap |
| 300 | Isometric view of the vaporization device shown at 200 |
| 400 | Under-side view of porous member cap 102 |
| 426 | Inner surface |
| 428 | Outer surface |
| 430 | Bottom surface |
| 432 | Outside chamfer |
| 434 | Optional heater cap bottom rim inside chamfer |
| 436 | Porous member cap orifice taper |
| 500 | Third embodiment of vaporization device of the present invention |
| 538 | Heater substrate |
| 540 | Substrate orifice |
| 542 | Optional opening |
| 544 | First inner wall |
| 546 | Second inner wall |
| 548 | Third inner wall |
| 600 | Fourth embodiment of the present invention |
| 650 | Outer ring |
| 652 | Inner ring |
| 654 | Inset |
| 656 | Cantilever spring |
| 658 | Second end |
| 660 | First end |
| 662 | First Opening |
| 664 | First cylindrical wall |
| 666 | Second cylindrical wall |
| 668 | Third cylindrical wall |
| 670 | Fourth cylindrical wall |
| 672 | Ledge |
| 674 | First opening |
| 676 | Pocket |
| 678 | Second opening |
| 680 | Inner cylindrical wall |
| 682 | Inner wall |
| 700 | Isometric view of the vaporizer shown in FIG. 6 |
| 784 | Heater |

-continued

| Reference Numerals Used in the FIGURES: | |
|---|---|
| 786 | Optional contact tab |
| 788 | Container |
| 790 | Top of inner ring 652; not visible in FIG. 6 |
| 792 | Top of inset 654; not visible in FIG. 6 |
| 794 | Inner wall |

DEFINITIONS

In the present specification and claims, reference will be made to phrases and terms of art which are expressly defined for use herein as follows:

When used with respect to similarity in composition, the term “substantially the same” as used herein means at least 60% similarity in composition; preferably greater than 70% similarity; more preferably greater than 80% similarity; and most preferably greater than 90% similarity in composition with a multicomponent liquid feed.

When used with respect to variation in composition, the term “substantially the same” as used herein means less than 40% variation in composition; preferably less than 30% variation; more preferably less than 20% variation; and most preferably less than 10% variation in composition from a multicomponent liquid feed.

With respect to dimensions of the present invention, it is understood that the term “diameter” as used herein refers to a cross-sectional length of an upper surface of a cylindrical porous member. For reference, see FIGS. 1, 2 and 4. The diameter of the present invention is typically less than 10 mm in diameter, preferably less than 9 mm in diameter, more preferably less than 8 mm in diameter, and most preferably less than about 7 mm in diameter. According to one preferred embodiment of the present invention, the diameter is about 5 mm.

DETAILED DESCRIPTION OF THE INVENTION

In one aspect, the present invention provides a device and technique for vaporizing liquids using low energy. In another aspect, devices of the present invention can be used to provide a visible plume of vaporized liquid with minimal rain-out. In yet another aspect of the present invention, the liquid vapor that is generated from a liquid feed to the inventive devices has very nearly the same scent perception as the original liquid feed to the device. This concept may be known as “scent fidelity.” The present invention is also concerned with a device that comprises no moving parts for the delivery of volatile compounds, typically but not necessarily limited to volatile organic compounds, either alone or blended in various formulations, without the use of aerosol propellants or mechanical pressurization. The present invention may also be used for the vaporized delivery of water and aqueous formulations.

According to one embodiment, an inventive apparatus relies on controllably delivering minimal bursts of energy to a portion of the device which, upon conversion of the energy to heat, induces a liquid feed to be drawn towards the heater through a series of capillary passageways. Liquid feeds suitable for use with the present invention comprise neat as well as multicomponent liquids. The induced force occasioned by the accumulation of the vaporized components projects them out of the device with a velocity sufficient to efficiently permeate enclosed spaces, for example, to render fragrancing of such spaces. The minimum use of energy results in minimal decomposition of liquid feed components, more uniform distribution of compound mixtures over time, significant decrease in energy use over time, and a consequent reduction in cost to consumers.

In its simplest form, a device according to the present invention may be regarded as comprising a heating element and a porous member in heat exchanging relation to the heating element. During operation of the heating member, liquid feed contacts a first face of the porous member and is drawn by capillary action to an opposing face of the porous member where it approaches the heating element. Heat from the heating element causes the liquid to be vaporized at interface regions between the heating element and the porous member, typically at a porous member cap. A buildup of vapor then takes place at the heating element-porous member interface as described above until sufficient pressure is reached in the vapor to propel it through an orifice in the heating element. The vapor is released in the form of a plume or jet at a pressure greater than that of the liquid feed. The heating element or heater of the inventive vaporizers need not remain in fixed engagement with the porous member at all times.

According to one embodiment of the present invention, the heating element, porous member cap, porous member and an optional wick may be provided as separable parts of the device. In a second embodiment of the present invention, the heating element is provided in a first portion of the device that can matingly engage a second portion of the device. The porous member is contained in the second, optionally disposable portion of the device. Also according to this second embodiment, the porous member cap may be located in either the first portion of the device with the heating element or in the second portion of the device with the porous member. The second portion of the device would also include a liquid feed and an optional wick disposed in liquid delivery relationship with the porous member. According to a third embodiment of the present invention, the heater and the porous member are not separable and are provided together as one unit along with a porous member cap. In any of the foregoing embodiments, replacement reservoirs of liquid may be used or exchanged with a liquid reservoir that may be initially provided with the inventive device.

A number of prior art vaporization devices are known, which are subject to assignment to the assignee of the present invention. These include: U.S. Pat. Nos. 5,692,095 and 5,870,525 to Young; U.S. Pat. Nos.: 6,162,046, 6,347,936, 6,585,509, 6,634,864 and 7,431,570 to Young, et al.; U.S. Ser. No. 11/355,461 to Rabin, et al.; U.S. Pat. No. 7,920,777 to Rabin, et al.; and U.S. Ser. No. 12/095,481 to Sellers, et al. In all of the foregoing, the geometric relationship among the heating source and one or more porous ceramic members comprising the devices can, for the most part, be characterized as stacked cylinders. In general, the stacked cylindrical layers all had nearly the same diameter such that the sides of the devices were continuous and even. Some of these foregoing vaporization devices were optimized for use with liquids such as fuels and other combustible materials, as for heating and lighting applications. Others of the above devices were developed for lower temperature applications such as might be used with water and aqueous compositions, an example of which would be for humidification purposes. In many of the foregoing examples, the vaporization devices described and claimed fulfilled one function or served one purpose as part of a multi-component system.

In prior art vaporizers in which peripheral glazes were used to form seals, a crack in the glaze was problematic at best and could instantly render the device useless. Depending upon the nature of the material being vaporized, the leak might or might not cause a failure of the device. Leaks that occurred that were not associated with cracked peripheral glazes were inconvenient or aesthetically undesirable such as those that might arise upon using the device for extended periods of time such as one to two months and longer. Thus, for heating, cooking or lighting applications in which a small leak occurred, the heat generated by a device might eventually evaporate any liquid fuel that would leak from the device. One consequence in terms of device operation, therefore, is a decrease in efficiency due to the incomplete vaporization of liquid feed; that is, the fuel lost to cooking, heating or lighting applications; or alternately, the water lost to humidification applications. Often, any leaks in the foregoing devices were not readily noticeable due to the manner in which the devices were operated and/or configured. Thus, inter- or intra-component leaks might not be apparent due to the masking effect of flames, light or heated currents of air emanating from the vaporizing device. In applications in which vaporization devices were used for moisture generation, for instance, leakage of water might not readily be noticeable due to the flow of air that surrounds the device and into which non-vaporized water may be entrained or carried along into humidification streams.

At some time during their lifetimes, many of the prior art vaporization devices described above leaked, that is, they exhibited leakage of liquid, vapor, or a combination of both liquid and vapor from the device. The leakage that was observed could best be described as sputtering, spitting, off-gassing, bubbling, foaming, oozing, or any combination of the foregoing. In some cases, the location of liquid and/or vapor leakage was intra-component, that is, along the periphery of one or more of the individual layers or members comprising the device. In other cases, leakage was observed as an inter-component phenomenon, that is, at the interface between two constituent layers of the device, such as between the heater and an adjacent layer of the device. At yet other instances, there may have been various combinations of intra- and inter-component leakage. As leakage is undesirable from aesthetic and/or efficiency perspectives, any leakage associated with the operation of vaporization devices is therefore problematic. Surprisingly, it has now been found with the inventive vaporizers described herein that by modifying the spatial geometry and/or the surface energy of certain component parts, any leakage formerly associated with vaporization devices for use with certain feedstocks or for certain applications may be virtually eliminated.

With the foregoing and other prior art vaporization devices in which a thin glaze, which was optimized for particular functions, may have been used to seal the perimeter of stacked components or to provide a housing for the device, the perimeter glaze was often difficult to apply during large-scale manufacturing processes. The perimeter glaze was also prone to cracking during use of the vaporization devices, which could ultimately cause the device to fail. In some instances, for example, cracking of the glaze would occur due to thermal stresses and differences in coefficients of thermal expansion between adjacent component layers. Cracks in the glaze would then permit seepage of liquid and give the impression that the device was leaking. In situations in which vaporizers were used with flammable or combustible materials, for instance, fracture of the glaze would render the device useless and potentially dangerous if leaking vapor were to catch fire. Camp stoves, lanterns and heaters are three examples of prior art vaporization devices in which perimeter glazes may have been used.

By contrast, due to the combination of the kinds of fittings and the compliant nature of the housing that is used in the present invention, the likelihood of cracking of the housing of vaporizers of the present invention can be greatly reduced. Moreover, as discussed below, in pulse mode operation, the instant invention more efficiently directs heat to the liquid being vaporized than many prior art vaporizers. One consequence of this is that the inventive devices are able to vaporize liquid with lower energy consumption over time.

Another aspect in which vaporizers of the present invention differ from certain prior art capillary vaporizers is that there are no springs or mechanical force generators used to apply compressive forces within the present invention. Instead, according to one embodiment, the present invention features a clearance fit connection between porous member 114 and housing 118 and a press fit between porous member cap 102 and housing 118. Thanks in part to the optimized porous member cap configurations described herein, press-fitting and clearance fits that are employed in the inventive vaporizers described herein provide the mechanical force necessary to matingly engage cap 102 with porous member 114. A separate mechanical force generator is therefore rendered unnecessary in the present invention, as the combination of press- and clearance-fittings within the housing fulfill that role. It should also be noted that the inventive porous member and porous member cap configurations described herein were developed to achieve a particular, desired pre-load. That is, in order to increase efficiency in heat exchange between the heater and the porous member, the pre-load on the porous member and the porous member cap should be greater than zero. One consequence of having a greater than zero pre-load is that it is not necessary to include springs to hold the vaporizer components in compressive relationship. This simplifies the manufacture, assembly and re-use of sub-assembly portions of the inventive vaporizers where desired, as is discussed in greater detail below.

Features of the present invention that may also be regarded as advantageous over air treatment vaporizers of the prior art include: 1) no moving parts; 2) minimal usage of energy over the period of payload delivery, thus reducing the carbon footprint associated with the use of the vaporizer; 3) no use of aerosol compounds, thus minimizing the use of solvent components; 4) the possibility for visibly observing delivery of the vaporizer payload; and 5) vapor projection throughout an enclosed space within minimal time.

Figure 1:
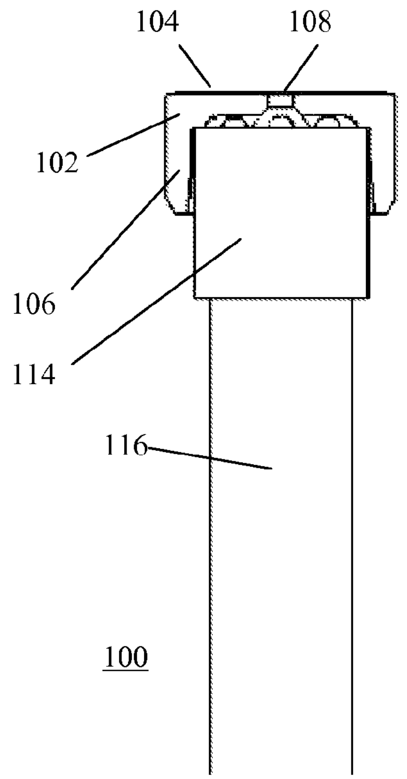
FIG. 1 is an illustration of a cross-section of a vaporizer according to an embodiment of the present invention.

Turning now to the accompanying Figures, a vaporization device according to one embodiment of the present invention may be represented by device 100 of FIG. 1. It should be noted that like numbers are used throughout the description to represent common elements. Accordingly, device 100 includes heat trace 104, porous member cap 102, porous member 114 and optional wick 116. Heat trace 104 is situated in heat-exchanging relationship with porous member cap 102. Porous member cap 102 further includes orifice 108, fins or projections 110 and channels 112. Porous member cap 102 may also include side wall 106.

Figure 2:
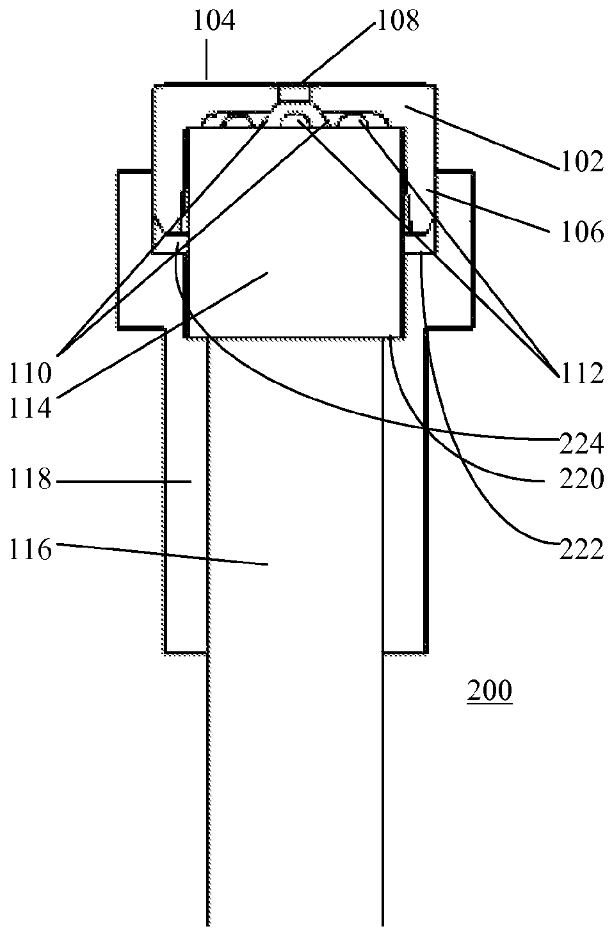
FIG. 2 is a cross-sectional illustration of a vaporizer according to a different embodiment of the present invention.
Figure 3:
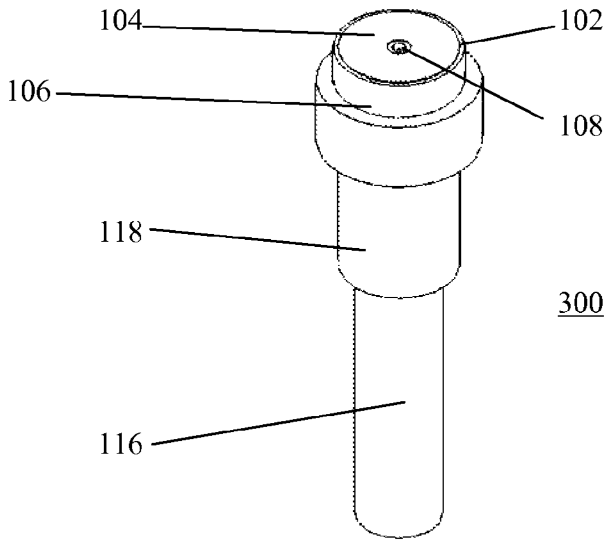
FIG. 3 is an isometric view of the vaporizer shown in FIG. 2.

An enlarged view of a vaporization device according to a different embodiment of the present invention is shown in at 200 in FIG. 2. Device 200 includes housing 118 in addition to heat trace 104, porous member 114, porous member cap 102 and optional wick 116. Heat trace 104, which is just visible at the upper portion of device 100 in FIG. 1 and at the upper portion of device 200 in FIG. 2, is more clearly visible in the isometric view of device 300 of FIG. 3. Housing 118 of device 200 also comprises first ledge 220 and second ledge 222. Porous member 114, together with optional wick 116, if present, rests upon first ledge 220 of housing 118. Porous member cap 102 with heat trace 104, situated at a surface of porous member 114 opposing that at which liquid is drawn into porous member 114, is situated within housing 118 such that side wall 106 of cap 102 encircles porous member 114. According to a preferred embodiment of the present invention, porous member cap 102 is press-fit into housing 118. Side wall 106 of cap 102 does not reach second ledge 222 of housing 118, thereby creating first gap 224. Gap 224 is thus bounded on a lower region and towards the outside by housing 118. Porous member 114 and the bottom surface of side wall 106 of cap 102 define the remaining two boundaries of gap 224 disposed towards the inside wall and at the top, respectively.

Figure 4:
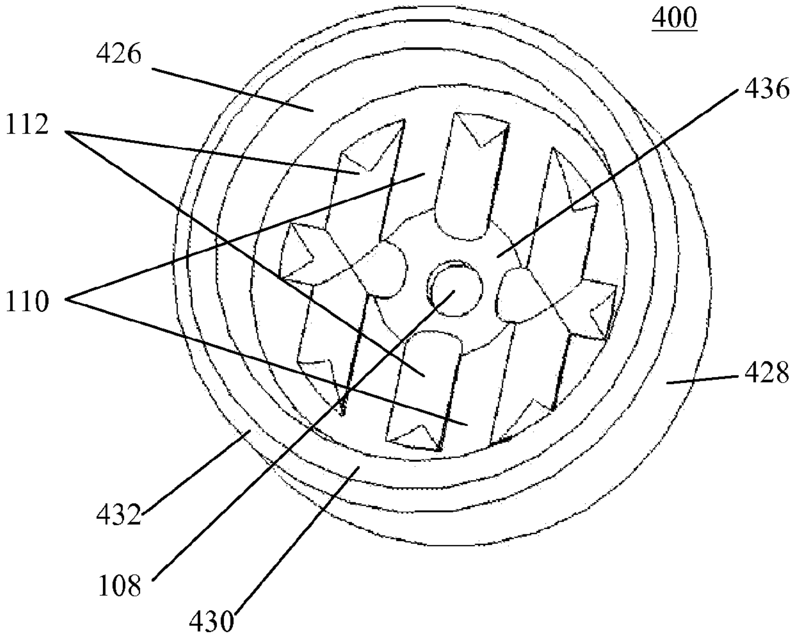
FIG. 4 is an illustration of the under side of a heater cap according to another embodiment of the present invention.

FIG. 4 provides a more detailed view of porous member cap 102 according to another embodiment of the present invention at 400. The perspective of cap 102 shown at 400 is that of an interior view; that is, from bottom surface 430 of side wall 106 of cap 102 looking towards orifice 108. Consequently, heat trace 104 is not visible in FIG. 4. Features of cap 102 that may be difficult to discern in FIGS. 1 and 2 include inner surface 426 and outer surface 428 of porous member cap 102, outside chamfer 432, and orifice taper 436, as well as already-described fins or projections 110 and channels 112. Side wall 106 of cap 102 may also optionally include inside chamfer 434, which is not shown in FIG. 4, but which is visible in device 500 in FIG. 5.

Figure 5:
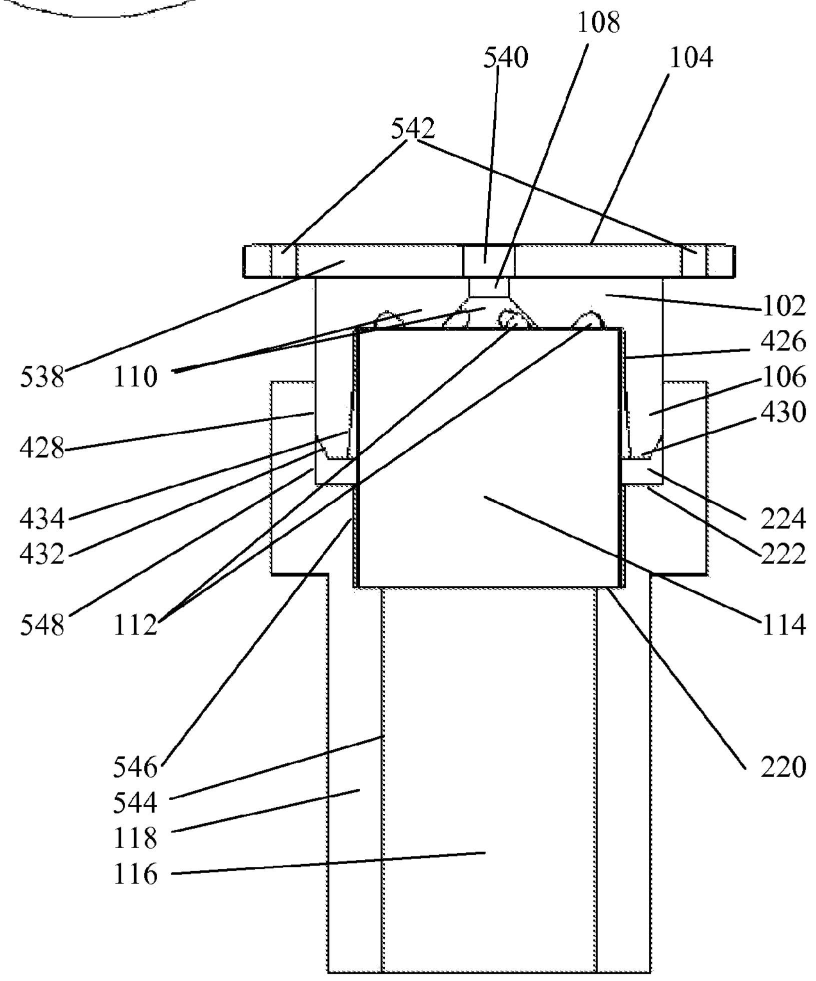
FIG. 5 is an illustration of a cross-section of a vaporizer according to yet another embodiment of the present invention.

A different embodiment of a vaporizer device according to the present invention is shown at 500 in FIG. 5. In this particular embodiment, the heater comprises heat trace 104 and supporting substrate 538. It should be noted that different heater configurations may be used with the present invention. In one embodiment, a heater provided for use with the present invention comprises heat trace 104, which is situated in direct heat-exchanging relationship with porous member cap 102, as described above and as illustrated at 100, 200 and 300. In a second heater configuration according to a different embodiment of the present invention depicted at 500 in FIG. 5, a heater comprises heat trace 104 disposed on one surface of substrate 538. An opposing surface of substrate 538 is disposed towards and makes intimate contact with porous member cap 102. Thus in device 500, substrate 538 is interposed between heat trace 104 and cap 102. Substrate 538 engages porous member cap 102 at a surface opposite that of heat trace 104 such that orifice 540 of substrate 538 is aligned in vapor releasing configuration with orifice 108 of cap 102.

Also shown in FIG. 5 are optional openings 542 in substrate 538, which may be provided as an accommodation, for instance, for connecting wires to or making soldering connections with heat trace 104. First, second and third inner walls 544, 546 and 548, respectively, of housing 118 are also shown. Inner wall 546 is clearance fit to porous member 114, while inner wall 548 is press-fit to porous member cap 102. Cross-sectional views of outside chamfer 432, optional chamfer 434 and bottom surface 430 of porous member cap 102 are also shown.

FIG. 6 shows a fourth embodiment of the present invention at 600. In this embodiment, a vaporizer similar to that shown at 500 is contained within, and disposed towards, the interior of outer ring 650, inner ring 652 and inset 654. Inner ring 652 further includes first cylindrical wall 664, second cylindrical wall 666 and third cylindrical wall 668. Fourth cylindrical wall 670 is partially obscured by inset 654. Element 656 is a cantilever spring that contacts heat trace 104 on substrate 538. The end of spring 656 that contacts heat trace 104 is depicted in 600 as a cup-shaped or ovoid-shaped first end at 660. Cantilever spring 656 extends from first end 660 across the top and a portion of the outer wall of inner ring 652 to second end 658. Second end 658 of cantilever spring 656 may optionally include opening 662 and may optionally extend outwardly and away from inner ring 652, as depicted at 600 in FIG. 6. As will be appreciated by those knowledgeable in the heater arts, cantilever spring 656 may also be used to provide power to heat trace 104 from an external source.

Also shown in FIG. 6 are: ledge 672 of inset 654; first opening 674 of inner ring 652; pocket 676, which is formed between outer ring 650 and inner ring 652 and provides a region to accommodate cantilever spring 656; second opening 678, which is situated above inset 654 and disposed towards the interior of inner ring 652; cylindrical wall 680, which is disposed towards the interior of outer ring 650; and inner wall 682, which is a portion of a groove cut into inset 654 that can receive a portion of cantilever spring 656 when it is not deflected upwards, as shown in FIG. 6.

Collectively, optional wick 116, porous member 114, porous member cap 102 and housing 118 together with a liquid reservoir or suitable feed supply, not shown in FIG. 6, may be regarded as together comprising a first sub-assembly, referred to herein as a lower vaporizer portion or base assembly. Components 650, 652 and 654 together with cantilever spring 656 may collectively be regarded as comprising a second sub-assembly, referred to herein as a head assembly or upper assembly.

Figure 7:
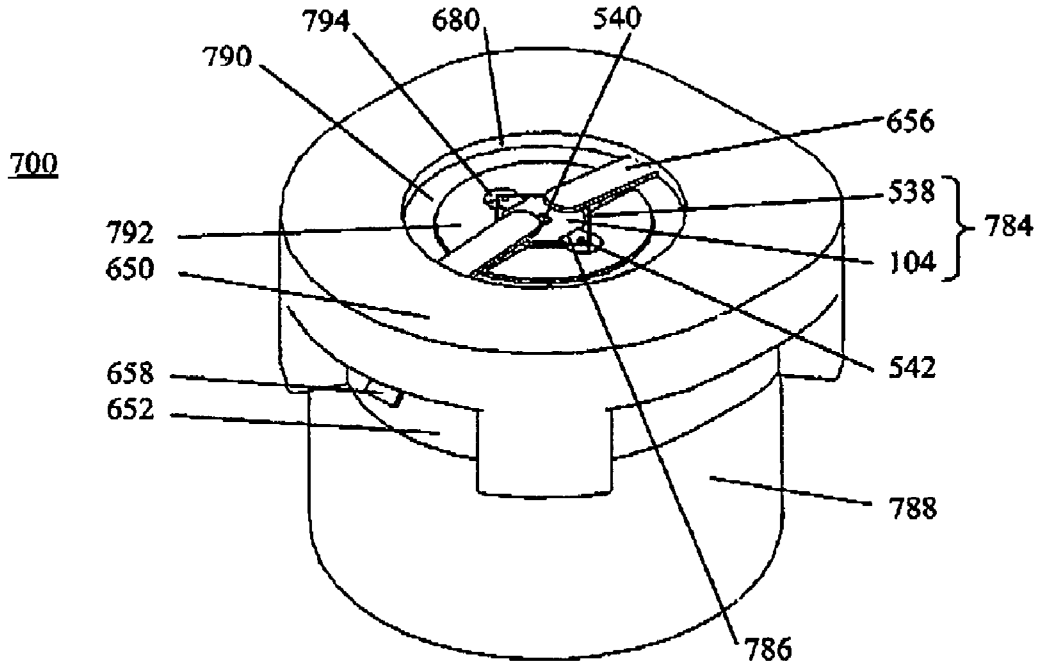
FIG. 7 is an isometric view of a vaporizer according to yet a different embodiment of the present invention.

It will be appreciated by study of FIG. 7 that element 656 is a cantilever spring that contacts heat trace 104 on substrate 538 via optional contact tab 786. In embodiments in which tab 786 is not present, cantilever springs 656 are in direct contact with heat trace 104. In contrast to the material of the resistive heat trace 104, optional contact tab 786 is preferably of a highly conductive, that is, a low resistive, material, including but not limited to: metals such as gold, silver and copper; and alloys such as tin-lead, silver-platinum and copper-nickel; as well as combinations thereof. Further, the material used for heat trace 104 and optional contact pad 786 should be chosen in order to ensure an integral bond that will resist higher temperatures during heating, as well as abrasion during replacement of the bottle of liquid actives.

In a unique aspect of the present invention, when the base assembly is removed from the head assembly, heater 784 in FIG. 7, which comprises heat trace 104 and substrate 538, is deflected in a downward direction by cantilever spring 656 through a portion of pocket 676 until substrate 538 comes to rest upon ledge 672 of inset 654. Heater 784 therefore remains behind within the head assembly for re-use whenever a base assembly is repositioned or replaced within inner ring 652.

To engage a lower vaporization portion with a head assembly for liquid refill, for transportation or for planned instances of non-use, container 788 shown at 700 in FIG. 7 containing a lower vaporization portion that is not visible in 700 may include one or more fittings for matingly engaging inner ring 652 at one or more cylindrical walls 664, 666 or 668 via a variety of techniques available to those knowledgeable in the connection arts. Thus, inner ring 652 and a lower vaporization portion may be engaged via the use of bayonet fittings, snap-lock fittings, threaded fittings, and the like. Other fittings such as glue or friction fittings, i.e., press-fittings, could also be used, although these would render it more difficult to separate the lower vaporization portion from the head assembly for re-use or recycle purposes.

The ability to remove a lower vaporization portion from a heater according to the present invention provides a number of advantages over vaporizers of the prior art. The separability of the heater: 1) permits the heater to engage numerous refill bottles, containers, liquid receptacles or reservoirs whenever it is inserted; 2) prevents the heater from imparting too much heat and possibly melting the housing or head assembly when not in use; and 3) allows the heater to be positioned securely within the head assembly whenever a refill bottle is not inserted into the assembly. The latter point is of importance especially in light of the type of handling and transportation that any of the inventive devices that incorporate a head assembly is likely to experience. The separability and ability to securely store the heater helps to protect the device from shocks and vibrations that are likely to be encountered during transportation.

It has been found that intrinsic properties such as boiling point, viscosity and surface tension of liquid actives as well as extrinsic conditions such as barometric pressure and ambient temperature can lead to oozing of liquid actives to be vaporized with a vaporizer. While being a significant aesthetic disadvantage, this effect also has significant functional disadvantages. For example, actives that might ooze or disperse over the heating surface can lead to charring upon heating, resulting in significant generation of malodors. Such oozing can further lead to contact of active organic compounds with other parts, which can lead to corrosion and disintegration of components. Finally, as the active liquid flows over the heat trace surface and beyond, disruption of electrical contact can result.

It has been found that by modifying the surface energy of the heat trace of the inventive vaporizers, significant reduction of the oozing of actives, in other words, the liquid being vaporized, can be realized with the present invention. Modification of the surface energy of the heat trace is achieved by using, applying, coating or incorporating a treatment medium with at least one of the heat trace and whatever vaporizer component is situated immediately adjacent to the heat trace, either during or subsequent to manufacture of the heat trace or component. Treatment media that are contemplated for use with the vaporizer devices of the present invention include perfluorinated compounds that are heat stable to at least 350° C. Examples of perfluorinated compounds that are appropriate for use with vaporizers of the present invention include polytetrafluoroethylene also written as PTFE, fluorinated ethylene propylene copolymer also written as FEP, perfluoro alkoxyalkane copolymer also written as PFA, ethylene tetrafluoroethylene copolymer also written as ETFE, and the like. According to one embodiment of the present invention, a treatment media is applied in the form of a coating. According to another embodiment of the present invention, a treatment media may be applied to an upper surface of heat trace 104, a lower surface of substrate 538 if present, an upper surface of porous member cap 102 if present, at the surface of orifice 108 in porous member cap 102 or the surface of orifice 540 in substrate 538, as well as combinations of any of the foregoing. When substrate 538 is present, a surface treatment preferably concerns the closest 10% of the area of heat trace 104 that surrounds orifice 540, more preferably the closest 50% of the area of heat trace 104 that surrounds orifice 540, and most preferably the closest 90% of the area of heat trace 104 that surrounds orifice 540.

For instances in which heat trace 104 directly contacts porous member cap 102 without an interposing substrate 538, surface modification of heat trace 104 can be effected by application of a surface treatment to an upper surface of heat trace 104, at orifice 108 of porous member cap 102, as well as combinations of either of the foregoing. When substrate 538 is not present, a surface treatment preferably concerns the closest 10% of the area of heat trace 104 that surrounds orifice 108 of porous member cap 102, more preferably the closest 50% of the area of heat trace 104 that surrounds orifice 108, and most preferably the closest 90% of the area of heat trace 104 that surrounds orifice 108. In either of the situations just described, that is with or without the presence of substrate 538 and regardless of the technique used for using, applying, coating or incorporating a treatment medium with a vaporizer of the present invention, the resultant surface energy of the treated surface should be less than about 30 dynes/cm, preferably less than about 25 dynes/cm, and more preferably less than about 20 dynes/cm. Discussions of the surface energy of various materials can be found at several places online, one of which is http://www.accudynetest.com/surface_energy_materials.html.

With regard to the present invention, is envisioned that application of surface modifying actives can be achieved through various means, including spraying, melting, and/or application via painting, rolling, screening, padding, or film transfer. It is also envisioned that interposition of a low-surface energy element within orifice 108 can serve a similar purpose of pre-venting oozing of liquid active across heat trace 104. While not preferred due to need for precise manufacture and assembly, such an element would also achieve the desired effect of interrupting the flow of liquid active across the top surface of the heat trace and beyond.

Alternate means for delivering energy to the vaporizers of the present invention can include: integrated power sources, exemplified by, but not necessarily limited to: heat traces, heaters, heat exchangers, inductive coils, resistive elements, etc.; electromagnetic radiation such as a lens to focus incident sunlight on the CFV; other incident light energy such as laser sources; microwave energy providers, etc.

According to one method of the present invention, assembly of a vaporizer device involves positioning a porous member into a housing and pressing down on the porous member until it reaches a stopping point in the housing, generally defined by a first ledge of the housing. The porous member is thereby clearance-fit into the housing. Once the porous member has been set into place within the housing, a porous member cap is placed about the porous member and press-fit into the housing, as it is not practical to press-fit one ceramic to another. Press fitting helps to prevent vapor from exiting the device at any location other than at the orifice, which is the desired point of vapor release.

During a press-fit engagement of the porous member cap to the housing, the housing expands to accommodate the porous member cap. Other types of connecting techniques that may be used with the present invention include snap fits, gluing, threaded connections, and welding. According to a preferred embodiment of the present invention the porous member cap is press-fit into the housing. According to another preferred embodiment of the present invention, therefore, the housing is comprised of a deformable material, in other words, one that is compliant or ductile. The housing may be fabricated from any material that does not decay, break down, decompose, stress-crack, dissolve or otherwise fail in the presence of volatile organics, fragrancing components, pharmaceutical, or insecticide compositions that may be used in accordance with the present invention. The housing must also be sufficiently thick so as to not crack or melt, given the amount of power supplied to the vaporizer. In one preferred embodiment, the housing is comprised of a plastic material such as polyethylene terephthalate, also written as PET. PET is an example of a material that can be used for the inventive vaporizer housing described herein in the presence of certain fragrance components such as phenyl derivatives, including, but not limited to: phenylethanol, eugenol, cinnamic aldehyde, vanillin and the like.

By comparison, materials that are suitable for use in the porous member and porous member cap of the present invention may be characterized as stiff and rigid. However, according to a preferred embodiment of the present invention, the porous member cap is allowed to expand and contract with the application and removal of heat without large stresses incurred by mating parts. In other words, the housing should not impart significant stresses to the porous member cap during heating or cooling cycles. According to a preferred embodiment, the porous member and porous member cap are comprised of a ceramic material. Note, however, that the porous member is preferably comprised of a porous material or porous ceramic, while the cap used to contain and partially surround the porous member, that is, the porous member cap, is preferably not comprised of a porous material.

It has been found that the porosity of the porous member plays an integral part in the successful delivery of liquid actives. Porosity can be defined as the void space within the innate ceramic material and is measured as a fraction of the material from 0-100%. Porosity of the material should be greater than about 25%, more preferably greater than about 40%, and most preferably greater than about 60%. Pore size, by contrast, can be defined as the mean dimensionality of the pores. In the extreme, pores can be visually detected, to the point of actually seeing channels coursing through the material. It should also be appreciated that there is a balance between the innate porosity of a ceramic material and its pore size. Without an innate porosity, a ceramic material would not allow liquid transport to occur therethrough. Should the pore size be too great, however, there would be a loss in capillary action and transport of liquid through the ceramic matrix would be inhibited. The structure of the ceramic material used for the porous member can be random with respect to the direction of material flow. Without being bound by theory, it is thought that the liquid active is transported via a tortuous path through the ceramic, in which the pores effectively communicate within the matrix. Such transport is aided by the aforementioned capillary action, and the net directionality of the flow is a result of the heating of the liquid actives and discharge of vapor at a surface of the porous member disposed opposite to the surface at which liquid actives enter the porous member.

Increasing the pore size can have profound effects on the efficiency of the system. Depending on directionality, pores may even act as an insulating layer within the porous member. In the extreme, channels can be realized purposely in the porous member matrix, for example, via an extrusion step followed by application of heat to solidify the ceramic. Although it may seem logical to have such pores, or channels, oriented in a direction parallel to the net flow of the liquid actives, it has been surprisingly discovered that the preferred directionality of such channels is actually perpendicular to the flow of the liquid actives. By so orienting the channels perpendicular to the flow of the liquid actives, heat transport downward through the porous member is minimized while liquid can still be transported through the remainder of the porous member matrix via the innate pores of the ceramic. Channeled ceramics can be obtained from a number of commercial sources, such as Corning, Inc., of Corning, N.Y., $GEO_2$ Technologies of Woburn, Mass., and Prince Advanced Ceramics of Yixing, China.

According to a preferred embodiment of the present invention as noted above, the porous member cap is comprised of a non-porous ceramic, preferably alumina. In another preferred embodiment, the alumina used for the porous member cap is characterized as fully-dense alumina. The porous member cap comes to rest within the housing and about the porous member before reaching a second ledge, which is located a short distance from the first ledge. First gap 224 is thus created between the bottom of porous member cap 102 and the top of second ledge 222 in housing 118 as shown in FIGS. 2 and 5. Within certain tolerances, regardless of machining or manufacturing techniques, first gap 224 permits intimate heat-exchanging contact between porous member cap 102 and porous member 114. The goal is also intimate contact between cap 102 and housing 118. If porous member cap 102 rested upon second ledge 222 before engaging porous member 114, there would not be intimate heat-exchanging contact between the cap 102 and porous member 114. Moreover, it is conceivable that vapor could undesirably emanate from the region in the absence of a tight press-fit between cap 102 and housing 118. The gap between the porous member cap, porous member and housing thus provides allowable tolerances for the relevant vaporizer parts.

The present invention dispenses volatile material in a very energy-efficient manner. Energy is saved through the application of intermittent power rather than by the use of continuous power to deliver a payload, unlike prior art vaporization devices. This is achievable in the present invention as the device is inherently efficient in transferring energy to the liquid to be vaporized. Rather than extraneously heating air or device parts that do not contribute to the successful vaporization of a liquid as in prior art devices, vaporizers of the present invention achieve efficient and intimate heat-exchanging contact among the component parts. This intimate heat-exchanging contact is attributable, for example, to the combination of press fitting and clearance fitting that successfully hold the porous member and porous member cap in tight, intimate contact within the housing. Consequently, energy is more efficiently transferred from the heater or heat trace to the porous member and thus to the liquid to be vaporized.

As a consequence of having low energy operating requirements, the devices of the present invention do need not to draw much energy when they are in use. Indeed, compared with many prior art devices that are used for disbursing fragrances, medicaments or insecticides, the vaporizers of the present invention utilize smaller quantities of energy per amount of liquid vaporized. As the devices of the present invention direct heat to the liquid being vaporized with greater efficiency than certain prior art vaporizers, variations in energy delivery to the heater can be contemplated. Thus, individual, repeated, pulsed, as well as pre-programmed or variable amounts of energy can be used for successful operation of the inventive devices described herein.

Vaporizers of the present invention are contemplated for use in situations in which the device controllably cycles on and off. Discrete, non-continuous operation permits the devices to cool off between deliveries, thus preventing overheating of the inventive housings. Non-continuous operation also minimizes potential degradation of any sensitive actives that might be present in the liquids used with the inventive vaporizers. Uses contemplated for the inventive vaporizing devices discussed herein include the delivery of pharmaceuticals and pharmaceutical compositions to an individual as well as the delivery of fragrancing formulations to rooms or small spaces. However, less intermittent or more continuous operation of the inventive vaporizers is also possible. While continuous operation of the inventive vaporizers might introduce too much material into small spaces in a short time—as with fragrancing or pharmaceutical applications—continuous operation could be desirable for insecticide delivery or other applications contemplated for use over larger areas or in situations that require more intense vapor delivery. With more continuous use or in instances where the vaporizer housings are less frequently permitted to cool down between vaporizer bursts, however, additional factors such as the difference between operating and ambient temperatures, nature of the housing material used in the vaporizer, etc., might need to be considered for successful operation of the vaporizer.

An example of a continually operated vaporizer of the prior art is one that is used for patient humidification purposes. These devices are run or operated continually, that is, they are said to be on all the time and therefore require large amounts of energy. Using a prior art humidifier at lower energies continually over longer periods of time might be acceptable for patient humidifiers, but would be untenable for pharmaceutical or fragrance applications. Delivery of either pharmaceuticals or fragrances continuously would provide too much of the material being vaporized to be efficacious or pleasant. As stated above, the present invention can use very low amounts of energy to provide intermittent bursts of vapor. By contrast, even if one were to operate a prior art vaporizer for shorter time segments as in fragrance applications to provide a burst of fragrance, the vaporizers of the present invention often use less total energy to vaporize comparable amounts of liquid.

There exists a further disadvantage of prior art vaporization devices that have high energy requirements. With some of the prior art vaporization devices described above, it has been observed that colored residue tends to form about the device orifice over time. It is postulated that this colored residue may indicate the breakdown of volatiles or fragrance components. This may further indicate the occurrence of fractionation or decomposition of components of multicomponent liquids, for example. Another explanation for this observation is settling out or condensation of liquid, which implies inefficient vaporization of the liquid feed. By contrast, devices of the present invention have much lower operating energy requirements than vaporizers of the prior art. Vaporizers of the present invention can thus be operated at lower energies over longer periods of time. Moreover, vaporization devices of the present invention may be operated at lower energy levels for the intermittent or discontinuous delivery of sensitive actives, thus overcoming the problem of fractionation or decomposition of actives as seen with continuous-operating devices of the prior art.

Operating parameters and energy requirements of several prior art vaporization devices were evaluated for comparison with devices of the present invention. Power requirements of the prior art devices discussed herein were located either on the actual device or on accompanying packaging. The first prior art device that was evaluated, Prior Art Device #1, was a Glade® PlugIns®, manufactured by S.C. Johnson & Son, Inc., of Racine, Wis. Operating without a fan, the device utilizes about 2 watts and is intended for use with a reservoir bottle containing 20.99 ml (about 0.71 fl. oz.) of fragrance liquid; refills last up to 60 days. This device therefore utilizes 10,368,000 Joules over 60 days to vaporize the fragrance liquid in the reservoir, which is equivalent to about 494 Joules/mg fragrance vaporized.

Prior art device #2 was a Glade® PlugIns® operating with a fan, also from S.C. Johnson & Son. This device utilizes about 3.7 watts per the stated rating. A reservoir bottle that comes with the device contains 20.99 ml (about 0.71 fl. oz.) of fragrance liquid; refills last up to 60 days. This system therefore utilizes 19,180,800 Joules over 60 days to vaporize fragrance, which is equivalent to about 914 Joules/mg fragrance vaporized.

The third prior art device that was evaluated, Prior Art Device #3, was a Febreze® NOTICEables™, from Procter & Gamble of Cincinnati, Ohio, that utilizes about 2 watts per the stated rating. The device includes a reservoir bottle that contains 25.99 ml (0.879 fl. oz.) of fragrance liquid; refills last about 30 days. This system therefore utilizes 5,184,000 Joules over 30 days; that is, about 199 Joules/mg to dispense the fragrance.

Prior Art Device #4 was an Airwick® Scented Oil Warmer manufactured by Reckitt Benckiser of Parsippany, N.J., that utilizes about 2.5 watts per its stated rating. This device includes a reservoir bottle that contains 20.99 ml (0.71 fl. oz.), with refills that last up to 60 days. This system therefore utilizes 12,960,000 Joules over 60 days; that is, about 617 Joules/mg for dispensing the fragrance.

Note that each of Prior Art Devices #1-4 described above operates continuously. That is, each of these devices constantly consumes power and remains in a state of continuous operation. By contrast, devices of the present invention, operating intermittently, were capable of delivering 40 mg of fragrance using only about 28 Joule/mg of fragrance vaporized; see Example 2 below. Stated another way, none of the devices of the prior art can vaporize as much material with as little energy as the devices of the present invention. Compared to the prior art vaporizers and dispensers described above, therefore, the device of the present invention exhibits greater energy efficiency.

The present invention also addresses certain inefficient aspects and disadvantages of prior-art plug-in units, such as those scribed in U.S. Pat. No. 6,909,840 to Harwig, et al., referred to herein as "Harwig": a) Harwig continuously heats a wick through current drawn from a plug; a stand-alone unit of the present invention uses microcircuitry to provide intermittent heating; b) Harwig has an air gap between the heating source and the wick, which results in significant energy loss; the present invention features a heating source in direct contact with the liquid being vaporized, with or without an optional wick; c) Harwig uses a wire, thin film or thick film heater that makes discrete contact with a wick only on points of contact and therefore is less energy efficient than the present invention, which has the advantage of heating an entire wicking surface; and d) The vapors generated by Harwig diffuse away from the unit; the vaporizers of the present invention feature a singular orifice in the heater for vapor egress.

There are several possible explanations for Harwig's energy inefficiency. First, it is possible that inefficient heating occurs due to the best mode heat source described, namely a wire. A one-dimensional heat source will not efficiently heat a two- or three-dimensional wick and a full emanating surface. Second, the thin- or thick-film heaters that are described in Harwig are deposited onto a ceramic substrate, thereby sealing any porosity of the ceramic. Fragrance cannot travel through Harwig's ceramic wick. If the heater contacts the top of the wick, the only location for fragrance to emanate from the device is through the sides of the wick, or at the edges of the heater-wick interface. Not only can this readily char the fragrance towards the center of the heater, it would likely char the fragrance at surfaces parallel to the heater's surface. Third, Harwig provides no place for the collection of vapor or any method by which pressurization can occur before vapor is released.

Perhaps it should not be surprising, therefore, that calculations of the energy requirements for the best mode described in Harwig reveal certain inefficiencies. At column 18, for instance, Harwig describes passing power drawn from wall current through a wire, the power shown in FIG. 10 therein ranging from 0.3 amps to 0.6 amps. Given a line voltage of 120 volts, this corresponds to 36-72 watts. Harwig then describes passing the current through the wire for one minute, resulting in a draw of 2160-4320 Joules. The data that Harwig presents in Table 1 in column 18 would seem to indicate that, under the best of conditions, they can deliver 815 micrograms per burst, resulting in an estimated energy use of 2,650-5,300 Joules/mg fragrance. As can be seen in the examples below, this is more than an order of magnitude less efficient than the best plug-in models, and two orders of magnitude less efficient than the vaporizers of the present invention.

In comparing the present invention to Harwig, it is noteworthy that the vaporizing devices of the present invention include at least one interposing layer, such as a porous member or vaporization layer. The interposing layer efficiently transfers momentary bursts of heat from the heater to the liquid feed being delivered to the heater or point of vaporization. The liquid is typically delivered to the heater through the porous member via capillary action. The bursts of heat are transferred with sufficient efficiency such that not more than 200 Joules of energy are necessary per milligram of volatile active delivered. The structure of any interposing layer according to the present invention is sufficiently porous to permit vapor that is generated at the interface of the heater and the interposing layer to accumulate and therefore build in pressure. The collected, pressurized vapor is then released at the orifice of the heater at a pressure greater than that of the incipient liquid feed, optionally in such a manner as to provide a visible mist or plume. While the devices of the present invention may be operated in virtually any direction, the configuration of the device allows egress of the pressurized vapor in a direction that is essentially perpendicular to the surface of the heater. In one aspect, vaporizer devices of the present invention can be used to vaporize a liquid with less than about 200 Joules of energy, preferably less than about 190 Joules of energy, more preferably less than about 180 Joules of energy and most preferably less than about 170 Joules of energy.

Operating a device of the present invention with too little power would result in the device functioning more like a warmer. That is, there would be insufficient power to convert the feed liquid to a gas and create an adequate pressure rise, such that the pressurization leads to a burst of vapor being emitted from the CFV. The combination of power adequate to vaporize a liquid feed to a gas and simultaneously build up sufficient pressure to release the gas as pressurized vapor is generally referred to herein as the "CFV effect." Thus with lower power, an insufficient amount of liquid feed would be vaporized, resulting in the inability to build sufficient pressure within the device. As a result, no plume of vaporized particles or fragrance would burst out of the device. In such instances, dribbling or dripping of the feed liquid might be observed instead of the more desirable pressurized wafting, streaming or bursting from the device. This is particularly important in pharmaceutical and drug delivery applications, where the vapor delivery space is small. For use with human patients, for example, the vapor delivery space may be regarded as the space within a patient's lungs. Thus, the use of a pharmaceutical composition with a device of the prior art, for instance, those described in U.S. Ser. No. 10/691,067 mentioned above, would lead to overdosing a patient.

Surprisingly, the present invention has been found to be a very efficient device for vaporizing neat liquids as well as multicomponent liquids. Examples of multicomponent liquids that may be vaporized by devices of the present invention include fragrance mixtures; pharmaceutical compositions; and so forth. Several examples are provided below.

EXAMPLE 1

A device of the present invention was used to vaporize 40 mg of liquid feed in a testing station. The total energy consumption required in order to vaporize the 40 mg of liquid was then calculated. It was found that the heating element used in the present invention drew 16 Watts during a four-second duration a total of six times during the course of one hour. During the same 60 minutes, a fan used to disperse the vaporized liquid drew 0.6 Watts over an eight second interval six times during the hour. The power requirement of the continuously operating test apparatus that was used in the course of the study was 0.2 Watts. The total energy usage could therefore be calculated based on the contributions of: 384 Joule for the heating element; 29 Joule for the fan; and 720 Joule for the test apparatus; for a total of 1133 Joule during one hour, or 28.3 Joule/mg fragrance vaporized.

EXAMPLE 2

A device of the present invention and a device of the prior art were both used to vaporize the same amount of material in one hour in order to compare the energy requirements of one with the other. Thus, by using a vaporizer of the present invention, it was found that 1,133 Joules of energy were required to dispense 40 mg of fragrance in one hour. By comparison, it was found that a prior art device, S.C. Johnson® Glade Scented Oil Fan®, operating at 3.7 Watts required an hour in order to disperse the same 40 mg of fragrance, for a total energy requirement of 13,320 Joules to vaporize the same amount of material as the present invention. In other words, the prior art device required more than ten times the amount of energy as the present invention to vaporize the same amount of liquid. Stated another way, the device of the present invention was twelve times more efficient in vaporizing the same volume of liquid in the same amount of time.

The results from Example 2 above show that the vaporizer of the present invention is at least ten times more energy efficient than a prior art device. The remarkable energy efficiency of the present device is perhaps even more noteworthy once it is understood that the present device was operated intermittently in Example 1, whereas the prior art device required continuous operation in order to vaporize the 40 mg of fragrance. Stated another way, heated wick products such as the Glade Scented Oil Fan cannot effectively vaporize fragrances using only 1,133 Joules of energy per hour.

EXAMPLE 3

In another aspect, and using a vaporizer of the present invention, it can be shown that it is possible to vaporize 40 mg/hr of un-pressurized liquid using less than 1200 Joules of energy. By analogy, therefore, it may be shown that the present invention can dispense on the order of 50 mg/hr of un-pressurized liquid using less than 1,500 Joules of energy; on the order of 60 mg/hr of liquid using less than 1,700 Joules; and on the order of 70 mg/hr of liquid using less than 2,000 Joules of energy. Each of these values represents considerable energy savings over prior art devices.

In cases where it is desired to vaporize less than 40 mg of liquid in an hour, or in order to best preserve the trueness of a fragrance delivered, the device of the present invention can be used to vaporize liquids with as little energy as 190 Joules per milligram of material. Much lower energy requirements may also be met. Thus, the device of the present invention can be used to vaporize liquids with less than 190 Joules/mg, preferably less than 150 Joules/mg, more preferably less than about 100 Joules/mg and most preferably less than about 50 Joules/mg.

With respect to fragrance applications, the present invention is capable of delivering a fragrance that delivers a profile that is more similar to the original formulated fragrance, as compared to many devices of the prior art. This may also be referred to as delivering a truer fragrance; a more true fragrance, a more true fragrance intention; better scent quality; less segregation of the fragrance components; and so forth.

Fragrances and perfumes, in particular, are described using a musical metaphor as having three notes, making the harmonious chord of the scent: top notes, middle notes and base notes. The notes unfold over time, with the immediate impression of the top note leading to the deeper middle notes, and base notes gradually appearing as the final stage. These notes are created carefully with knowledge of the evaporation process of the perfume.

Top notes are scents that are perceived immediately on delivery of a perfume or fragrance. Top notes consist of small, light molecules that evaporate quickly: they form a person's initial impression of a perfume and thus are very important in the selling of a perfume. The scents of this note class are usually described as fresh, assertive or sharp. The compounds that contribute to top notes are strong in scent, very volatile, and evaporate quickly. Citrus and ginger scents are common top notes. Top notes may also be referred to as head notes.

Middle notes are the scents of a perfume or fragrance that emerge after the top notes dissipate. Middle note compounds form the heart or main body of a perfume and act to mask the often, unpleasant initial impression of base notes, which become more pleasant with time. Not surprisingly, the scent of middle note compounds is usually more mellow and "rounded." Scents from this note class appear anywhere from two minutes to one hour after the application of a perfume. Lavender and rose scents are typical middle notes. Middle notes are also called heart notes.

Base notes are the scent of a perfume or fragrance that appear after the departure of middle notes. Base and middle notes together are the main theme of a perfume. Base notes bring depth and solidity to a perfume. Compounds of this class are often the fixatives used to hold and boost the strength of the lighter top and middle notes. Consisting of large, heavy molecules that evaporate slowly, compounds of this class of scents are typically regarded as rich and deep and are usually not perceived until 30 minutes after the application of the perfume or during the period of perfume dry-down. Some base notes can still be detectable in excess of twenty-four hours after application, particularly the animalic notes.

In a multicomponent mixture of volatiles, vaporizers of the present invention are capable of delivering olfactory elements in substantially the same ratio as the liquid in which they are formulated. Thus, the ratio of top notes to middle notes to base notes stays truer over time. This represents an advantage over certain forms of prior art devices such heated wicks, which are described and characterized in four prior art examples discussed above. Operating at higher energies, the prior art devices cause greater segmentation of the fragrance components that are to be volatilized. Over time, this results in less and less of a true fragrance compared to that of the original liquid feed. Conversely, if the prior art devices were provided with the lower energy levels associated with the present invention, they would not be able deliver enough fragrance over time.

It has been noted by impartial observers that the devices of the present invention produce a scent that is un-segmented by the heating member. With heated wick diffusers of the prior art, for instance, the more volatile components tend to move up a wick faster than the less volatile components. Hence, the character of the scent changes over the lifetime that the heated wick diffuser is in use.

One example of a portable apparatus for dispersing a liquid composition such as fragrances and insecticides in vapor form according to one embodiment of the present invention, therefore, includes:

a) a head assembly, further comprising a heater in electrical communication with a source of electrical power; and b) a removable base assembly, further comprising:

i) optionally, a reservoir for containing a liquid composition to be dispersed;

ii) a fitting for mounting the base assembly to the head assembly; and iii) a housing including a porous member cap, a porous member and an optional wick, the porous member cap being press-fit into the housing;

wherein the head assembly communicates with the base assembly for delivering heat to the composition in order to vaporize the composition at the porous member cap for release through an orifice in the heater that is in vapor communication with an opening in the porous member.

By utilizing the invention described herein, it has been found that difficulties experienced in prior art devices can be overcome. A summary of several of the improvements and features of the devices of the present invention as compared to prior art capillary vaporizer devices are now discussed. First, as compared to heated wick electrical diffusers of the prior art, the present invention features the advantages of: a) visible mist or plume to provide a cue of fragrance delivery; b) greater control over delivery rate and dosage ability; c) uniform vaporization of total fragrance mixtures; and d) from a safety perspective, less of a fire risk. That is, inventive vaporizers described herein require less energy and remain cool to the touch most of the time. Prior art electrical heated wick diffusers remain hot or are heated most, if not all, of the time they are in use.

In comparison to scented reed diffusers, the present invention: a) can emit a visible mist or plume to provide a visible cue of fragrance delivery, unlike reed diffusers which do not; b) imparts a better scent impact and perception by providing a fine mist of particles that can be dispersed by local air turbulence or via the use of a small fan; and c) is advantageous from a safety standpoint, as the liquid feed cannot spill from the device while in use. Fans that use less than about 0.5 watts and have a footprint less than about 10 $cm^2$ are an example of what is meant by a small fan. Third, as compared to fragrance oil warmers of the prior art, the inventive vaporizers described herein produce no soot or smoke, both of which are linked to environmental issues. Moreover, the inventive vaporizers provide prolonged fragrance delivery. The present invention can deliver comparable quantities of starting material over the course of weeks and even months, whereas prior art oil warmers may only run for hours.

By comparison with propellant-based dispensers, either of the manual or automated variety, the inventive vaporizers described herein are advantageous for the following reasons: a) there is no use of aerosol propellants; b) reduction of waste streams, as the present invention does not use dispensers, cartridges or canisters that are bulky and take up significant space upon disposal, as compared to the compact size of the vaporizers of the present invention; c) provides a fine mist of particles that can be dispersed by local air turbulence or fan with no rain-out, as is often observed with propellant-based dispensers; d) by eliminating propellants, a greater percentage of the vaporization composition can be devoted to essential oils, thus potentially resulting in more esthetically pleasing scents and potential reductions in packaging requirements. With respect to piezoelectric devices and pumps and nebulizers, the inventive vaporizers of the present invention feature no moving parts; are quiet during operation; and are compact in size.

Vaporizers of the present invention are well-suited to deliver fragrances into the atmosphere. Fragrances, also known as perfumes, are mixtures of fragrant essential oils and aroma compounds, fixatives, and solvents used to give the targeted objects, such as living spaces, a pleasant smell. The olfactory nature of the essential oils and aroma compounds vary widely, but are traditionally classified into categories such as: a) single floral, fragrances that are dominated by a scent from one particular flower, called a soliflore in French; b) floral bouquet, containing the combination of several flowers in a scent; c) ambery, a large fragrance class featuring the scents of vanilla and animal scents together with flowers and woods. Fragrances of this class can be enhanced by camphorous oils and incense resins, which bring to mind Victorian era imagery of the Middle East and Far East; d) woody, for fragrances that are dominated by woody scents, typically of sandalwood and cedar. Patchouli, with its camphoraceous smell, is commonly found in these perfumes of this class; e) leather, a family of fragrances which features the scents of honey, tobacco, wood and wood tars in its middle or base notes and a scent that alludes to leather; f) chypre, meaning Cyprus in French, this class includes fragrances built on a similar accord consisting of bergamot, oakmoss, patchouli, and labdanum; g) fougère, which means Fern in French, this class is built on a base of lavender, coumarin and oakmoss.

Since 1945, due to advances in the technology of perfume creation, that is, compound design and synthesis, as well as due to the natural development of styles and tastes, new categories have emerged to describe more modern scents, such as: h) bright floral, which combines the traditional single floral and floral bouquet categories; i) green, a lighter and more modern interpretation of the Chypre type; j) oceanic/ozone, the newest category in perfume history, appearing in 1991 with Christian Dior's Dune. This is a very clean, modern smell leading to many of the modern androgynous perfumes; k) citrus or fruity, an old fragrance family that until recently consisted mainly of freshening eau de colognes due to the low tenacity of citrus scents. Development of newer fragrance compounds has allowed for the creation of primarily citrus fragrances; and l) gourmand: scents with "edible" or "dessert"-like qualities. These often contain notes like vanilla and tonka bean, as well as synthetic components designed to resemble flavors.

For mixtures of ingredients that are contemplated for use with the present invention, it is preferred, but not mandatory, that fragrance components have similar boiling points. It is more preferred that their boiling points are within ±50° C. of a median value, and most preferred that they are within ±25° C. of a median value. It is contemplated that a solvent or combination of solvents would be desirable to incorporate in order to extend the fragrance mixture, or to lessen the olfactory impact of the fragrance mixture. If a solvent or combination of solvents is incorporated, it is preferred that at least 50% of the composition is composed of the solvent or combination of solvents and that the solvents render essentially no fragrance impact to the liquid mixture. It is also contemplated that it might be desirable to formulate a liquid mixture comprising solely olfactory active ingredients, without a solvent carrier.

From the discussion found on the internet at http://en.wikipedia.org/wiki/Solvent, a solvent is described as a liquid that dissolves a solid, liquid, or gaseous solute, resulting in a solution. The most common solvent in everyday life is water. Most other commonly-used solvents are organic, that is, carbon-containing solvents. Solvents usually have a low boiling point and evaporate easily or can be removed by distillation, thereby leaving any dissolved substances behind. Solvents contemplated for use with the vaporizers of the present invention should therefore not react chemically with any dissolved compounds; they should be inert. Solvents can also be used to extract soluble compounds from a mixture; the most common example of which is the brewing of coffee or tea with hot water. Solvents are usually clear and colorless liquids, and while many may have a characteristic odor, it is envisioned that solvents as envisioned for this discussion will impart minimal contribution of their own to the characteristic of the fragrance.

Solvents can be used to dilute actives, such as fragrances, that are contemplated for use with vaporizers of the present invention in order to decrease their olfactory impact as stated above. Solvents can modify the innate dispensing characteristics of solutions used with the vaporizers in order to mitigate the sensory perception of active components in a mixture. The solvents useful in this invention are organic solvents with a vapor pressure of at least 0.001 mm Hg at 25° C. and a solubility of at least 1 g/100 ml water. The upper limit of vapor pressure for solvents preferred for use with the present invention appears to be about 100 mm Hg at 25° C. Vapor pressure is a useful measure for determining the applicability of a given solvent, since it is desirable to select solvents for use with devices of the present invention that volatilize sufficiently so as minimize or eliminate visible residue. Organic solvents selected for use with the present invention are preferably selected from among: alcohols; glycols and glycol ethers, including ethylene glycol monobutyl ether, ethylene glycol monopropyl ether, propylene glycol monopropyl ether, propylene glycol monobutyl ether and isoparaffins; as well as mixtures of any of the foregoing. Amines, ketones, ethers, hydrocarbons, halides as well as combinations of any of the foregoing may also be used alone or in combination with any of the previously-mentioned organic solvents in the devices of the present invention. According to one embodiment of the present invention, glycol ethers, which have particularly good volatilization and solubilization characteristics, may be useful as organic solvents.

In using devices of the present invention, it has been found that neat or multicomponent liquids that have boiling points below about 150° C. give rise to vaporization plumes that are difficult to be perceived by the unaided eye. Without being bound by theory, it is postulated that the boiling point of a liquid that is being vaporized must be high enough such that cooling of the vapor upon exposure to ambient air allows the vaporized liquid to condense to produce a visibly satisfying plume, without readily condensing into droplets large enough to cause aerosol rain-out or wash-out. Preferred median droplet sizes are on the order of five microns or less. Aerosol rainout is understood herein to refer to the growth of cloud droplets on aerosol particles and the eventual removal of the aerosol particle to the surface by precipitation. Aerosol washout is understood herein to refer to the coagulation of aerosol particles and the precipitation of the resulting agglomerates when particles precipitate and subsequently fall to the ground. Solvents such as ethanol and lower-boiling paraffins, that is, those having boiling points less than about 140° C., while not excluded from use with the inventive vaporizers, are not preferred for use with vaporizers of the present invention whenever a visible plume of vapor is desired. Whenever observation of a visible plume is desired, the boiling point of liquid compositions used with devices of the present invention are preferably above about 150° C., more preferably above about 175° C., and most preferably above about 200° C.

In the course of the present invention, it has also been found that when a solvent is used to dilute a fragrance mixture to be vaporized, there exists a correlation between consumer-preferred performance attributes, the amount of solvent used to dilute the fragrance, and the boiling point of the solvent. Interestingly, for solvents having boiling points above approximately 215° C., there does not seem to be a limit in the percentage amount of solvent that can be used. One solvent preferred for use with the inventive vaporizers for fragrancing applications is diethylene glycol monopropyl ether, available commercially under such trade names as: the DP series of Dowanol™ DP from Dow Chemical Company; the DP series of Arcosolv® from Lyondell Chemical Company; and the DP series of Eastman from Eastman Chemical Company. Solvents having boiling point below approximately 215° C. should be limited in formulations to less than about 20 percent of the composition by weight to generate the most aesthetically pleasing plume.

It has been found that there is a high correlation between surface tension of the liquid mixture and its consequent propensity to cause spitting, popping, and residue formation on the surface supporting the inventive vaporization devices. As such, it is preferred that the surface tension of the liquid mixture be less than about 40 dynes/cm (40 mN/m), more preferably below 37 dynes/cm (37 mN/m), and most preferably below about 35 dynes/cm (35 mN/n).

It is preferred to limit the total amount of solvent that is used with fragrance formulations in the instant inventive vaporizers to less than about 90%, more preferably less than about 75%, and most preferably less than about 50% of the total composition by weight. Moreover, some compositions contemplated for use with the vaporizers of the present invention may not contain any solvent. A preferred range for the total amount of solvent from any source that is contemplated for use in compositions and formulations with vaporizers of the present invention is about 0-50%.

A number of fragrance and solvent compounds were evaluated for their ability to present a consumer-relevant delivery of actives. Individual components, as well as mixtures, were assessed for key attributes of boiling points, viscosity, and surface tension. These liquid samples were then placed within the inventive device, and assessed for consumer-relevant attributes such as burst response, plume quality, spitting and lingering on a 1-5 scale. A rating of 3 or above is considered acceptable. Explanations of each of the four attributes used in the evaluations are provided in Table 3; results of the actual evaluations are presented in Table 4 below.

TABLE 3

| Description of Attributes and Ratings Used in Fragrance Evaluations | | | | |
|---|---|---|---|---|
| | Attribute | | | |
| | Burst Response | Plume Quality | Spitting | Lingering |
| | Description | | | |
| Rating | How quickly plume starts after power-on of device | Shape and force of plume emitted | Observation of popping, droplets | How long plume continues after power-off of device |
| 1 | Very slow response | Wispy plume | Significant spitting | Prolonged pluming |
| 5 | Immediate visual cue | Forceful plume | No spitting | Sharp cut-off |

TABLE 4

Evaluations of Fragrances and Solvents Dispensed with Vaporizers of the Present Invention

| Sample | Boiling Point (° C.) | Viscosity (mPa-s) | Surface Tension (dyne/cm) | Burst Response | Plume Quality | Spitting | Lingering |
|---|---|---|---|---|---|---|---|
| Fragrances, Fragrance Components | | | | | | | |
| Linalool | 198 | 4.5 | 21.0 | 3 | 3 | 4 | 4 |
| Lime-Coconut Fragrance | 170-198 | 2.8 | 32.1 | 4 | 4 | 4 | 5 |
| Cornmint Oil | 209 | 9.2 | 32.3 | 3 | 4 | 5 | 3 |
| Peppermint Oil | 210 | 8.5 | 32.3 | 5 | 4 | 5 | 5 |
| Lavender Fragrance | 198-232 | 4.8 | 32.6 | 5 | 4 | 3 | 5 |
| Herbal Spice Fragrance | 176-215 | 6.0 | 32.7 | 5 | 5 | 4 | 5 |
| Thyme Oil | 195 | 3.5 | 33.4 | 5 | 5 | 4 | 5 |
| Phenylethanol | 218 | 7.6 | 44.0 | 4 | 4 | 2 | 5 |
| Solvents | | | | | | | |
| Isopar M | 223-254 | 2.0 | 26.4 | 3 | 3 | 4 | 4 |
| Diethylene glycol monobutyl ether | 230 | 4.7 | 33.8 | 4.5 | 4.5 | 5 | 4.5 |
| Diethylene glycol monopropyl ether | 216 | 4.0 | 34.5 | 5 | 5 | 5 | 5 |
| Propylene Glycol | 188 | 46.0 | 40.9 | 4 | 5 | 3 | 4 |

As noted above, it has been found that when a solvent is used to dilute a fragrance mixture, there is a correlation between consumer-preferred performance attributes, the amount of solvent used to dilute the fragrance, and its boiling point. As such, there does not seem to be a limit for solvents with boiling points above approximately 215° C. For solvents with boiling point below approximately 215° C. should be limited to less than about 20 percent of the composition by weight to generate the most aesthetically pleasing plume. As an example, typical fragrances were diluted with the solvents: diethylene glycol monopropyl ether, having a boiling point of 216° C.; an isoparaffinic solvent, Isopar M, having a boiling range of 223-254° C.; and propylene glycol, having a boiling point of 188° C.

TABLE 5

Evaluations of Neat and Diluted Fragrances Dispensed with Vaporizers of the Present Invention

| Sample | Boiling Point of Neat Solvent (° C.) | Burst Response | Plume Quality | Spitting | Lingering |
|---|---|---|---|---|---|
| Sage Fragrance | n.a. | 4 | 4 | 5 | 3 |
| Sage + 20% Isopar M | 223-254° C. | 5 | 3 | 4 | 3 |
| Sage + 40% Isopar M | | 5 | 4 | 5 | 4 |
| Sage + 60% Isopar M | | 5 | 3 | 5 | 5 |
| Sage + 80% Isopar M | | 5 | 4 | 5 | 5 |
| Sage Fragrance | n.a. | 4 | 4 | 5 | 3 |
| Sage + 20% Propylene Glycol | 188° C. | 3 | 3 | 4 | 3 |
| Sage + 40% Propylene Glycol | | 2 | 2 | 5 | 3 |
| Sage + 60% Propylene Glycol | | 2 | 2 | 5 | 4 |

TABLE 5-continued

Evaluations of Neat and Diluted Fragrances Dispensed with Vaporizers of the Present Invention

| Sample | Boiling Point of Neat Solvent (° C.) | Burst Response | Plume Quality | Spitting | Lingering |
|---|---|---|---|---|---|
| Sage + 80% Propylene Glycol | | 5 | 4 | 3 | 4 |
| Peppermint Fragrance | n.a. | 4 | 4 | 2 | 4 |
| Peppermint + 20% Di-ethylene glycol monopropyl ether | 215° C. | 5 | 5 | 5 | 5 |
| Peppermint + 40% Di-ethylene glycol monopropyl ether | | 5 | 4 | 5 | 5 |
| Peppermint + 60% Di-ethylene glycol monopropyl ether | | 5 | 5 | 3 | 5 |
| Peppermint + 80% Di-ethylene glycol monopropyl ether | | 4 | 4 | 3 | 5 |
| Peppermint Fragrance | n.a. | 4 | 4 | 2 | 4 |
| Peppermint + 20% Ethanol | 78° C. | 5 | 5 | 3 | 4 |
| Peppermint + 40% Ethanol | | 5 | 5 | 2 | 5 |
| Peppermint + 60% Ethanol | | 5 | 5 | 1 | 4 |
| Peppermint + 80% Ethanol | | 5 | 4 | 1 | 3 |

From the results presented in Table 5 above with respect to solvents having boiling points below about 215° C., it can be seen that it is preferable to limit the use of such solvents to less than about 20% by weight of the composition.

The apparatus and methods described herein are useful for the treatment of small areas, either indoor or outdoor, for air fragrancing, odor elimination, treatment of insects or pests, air sanitization, air and surface antibacterial or antimicrobial treatment, administration of personal pharmaceuticals, medicinal actives, medicaments, aromatherapeutics, as well as other ambient air or surface modification by way of gas, vapor or droplet distribution.

The present invention has been described above in detail with reference to specific embodiments, Figures, Tables and Examples. These specific embodiments should not be construed as narrowing the scope of the invention, but rather as illustrative examples. It is to be further understood that various modifications and substitutions are anticipated and may be made to the described vaporization devices and apparatus, as well as to materials, methods of manufacture and use, without departing from the broad spirit or scope of the invention contemplated herein. The invention is further illustrated and described in the claims, which follow.

What is claimed:

1. A method for generating a vapor from a liquid, comprising using a vaporization apparatus to vaporize the liquid, wherein the apparatus requires less than 200 Joules per milligram of liquid vaporized, preferably less than 190 Joules of energy per milligram of liquid vaporized, more preferably less than 180 Joules of energy per milligram of liquid vaporized and most preferably less than 170 Joules of energy per milligram of liquid vaporized, wherein the vaporization apparatus comprises a heater, a porous member cap and a porous member matingly configured for heat transfer between the heater and the porous member, wherein the porous member cap includes a side wall 106 for engaging the porous member at points along at least two surfaces, the porous member cap also including at least one further 110 and at least one channel 112 disposed at an interface with the porous member and further wherein a pre-load on the porous member cap and the porous member is greater than zero.

2. The method of claim 1, wherein the liquid contacts a first face of the porous member and is drawn by capillary action to an opposing face of the porous member where it approaches the heater, heat from the heater causing the liquid to be vaporized at interface regions between the heater and the porous member such that a buildup of vapor takes place at the interface regions, thereby causing vapor released through an orifice in the vaporization apparatus to exhibit a pressure greater than that of the liquid.

3. A method for vaporizing a multicomponent liquid to a pressure greater than that of a multicomponent liquid feed, comprising:

a. providing a liquid feed to a vaporizer; and b. vaporizing the liquid to generate a multicomponent vapor;

wherein the multicomponent vapor exhibits a composition that is substantially the same as that of the multicomponent liquid feed; and wherein the vaporizer comprises a porous member, a porous member cap, a heater, a housing, and optionally a wick, wherein the heater and the porous member cap are matingly configured for heat transfer between the heater and the porous member, wherein the porous member cap includes a side wall 106 for engaging the porous member at points alone at least two surfaces, the porous member cap also including at least one fin 110 and at least one channel 112 disposed at an interface with the porous member, and further wherein a pre-load on the porous member cap and the porous member is greater than zero.

4. The method of claim 3, wherein the nature of the connection between the porous member and the housing is characterized as a clearance fit and the nature of the connection between the porous member cap and the housing is characterized as a press-fit.

5. The method of claim 3, wherein the composition of the multicomponent vapor exhibits at least 60% similarity in composition; preferably greater than 70% similarity; more preferably greater than 80% similarity; and most preferably greater than 90% similarity in composition with the multicomponent liquid feed.

6. The method of claim 3, wherein the composition of the multicomponent vapor exhibits less than 40% variation in composition; preferably less than 30% variation, more preferably less than 20% variation and most preferably less than 10% variation in composition from that of the multicomponent liquid feed.

7. A method for generating a vapor from a liquid, comprising:

a) introducing a liquid feed to a vaporizer, the liquid feed characterized as having a first composition; and b) vaporizing the liquid feed and expelling the resulting vapor, the vapor characterized as having a second composition;

wherein the first composition and the second composition are substantially the same, wherein the vaporization apparatus comprise a heater, a porous member cap and a porous member matingly configured for heat transfer between the heater and the porous member, wherein the porous member cap includes a side wall 106 for engaging the porous member at points along at least two surfaces, the porous member cap also including at least one fin 110 and at least one channel 112 disposed at an interface with the porous member, and further wherein a pre-load on the porous member cap and the porous member is greater than zero.

8. The method of claim 7, wherein the second composition exhibits at least 60% similarity with the first composition; preferably at least 70% similarity; more preferably at least 80% similarity; and most preferably at least 90% similarity with the first composition.

9. The method of claim 7, wherein the second composition exhibits no more than 40% variation from the first composition; preferably less than 30% variation; more preferably less than 20% variation; and most preferably less than 10% variation from the first composition.

10. A method for dispensing a liquid formulation in the form of a vapor, comprising the steps of:

a. providing a liquid formulation having a first pressure in a container, the liquid formulation having a viscosity of less than about 100 mPas-sec and a surface tension less than about 40 dynes/centimeter;

b. delivering the liquid formulation from the container to a heater of a vaporizer by capillary action; and c. vaporizing the liquid at the heater of the vaporizer such that the vaporized liquid experiences a pressure increase and is released as a vapor at an orifice of the vaporizer at a second pressure that is greater than that of the first pressure, wherein the vaporizer comprise a heater, a porous member cap, a porous member and a housing matingly configured for heat transfer between the heater and the porous member wherein the porous member cap includes a side wall 106 for engaging the porous member at points along at least two surfaces, the porous member cap also including at least one channel 112 and at least one fin 110 disposed at an interface with the porous member, and further wherein a pre-load on the porous member cap and the porous member is greater than zero.

11. A method for dispensing a liquid formulation, comprising the steps of:

a. providing a liquid formulation in a container, the liquid formulation having a viscosity of less than about 100 mPas-sec and a surface tension less than about 40 dynes/centimeter;

b. delivering the liquid formulation from the container to a heater of a device by capillary action; and c. driving, by means of electric current, the heater, wherein the heater is matingly configured to a porous member such that the heater transfers heat to the porous member and vaporizes the liquid formulation, causing pressure buildup of vaporized liquid at an interface between the porous member and the heater, the heater being formed with an orifice, and subsequently releasing the vapor at a pressure greater than that of the liquid through the orifice;

wherein the liquid formulation is dispensed with uniform consistency over extended periods of time, wherein the device further comprises a porous member cap and a housing, wherein the porous member cap includes a side wall 106 for engaging the porous member at points along at least two surfaces, the porous member cap also including at least one fin 110 and at least one channel 112 disposed at the interface with the porous member, and further wherein a pre-load on the porous member cap and the porous member is greater than zero.

12. A method for dispensing a liquid formulation, comprising the steps of:

a. providing a liquid formulation to a vaporizer, the liquid formulation having a viscosity of less than about 100 mPas-sec and a surface tension less than about 40 dynes/centimeter; and b. vaporizing the liquid formulation to a vapor having substantially the same composition as the liquid formulation using a vaporizer;

wherein the vapor is dispensed by the vaporizer with uniform consistency over extended periods of time; wherein the energy consumed by the vaporizer is less than about 150 Joules per milligram of material vaporized; and wherein the vapor is released at a pressure greater than that of the liquid;

wherein the vaporizer comprises a heater, a porous member cap and a porous member matingly configured for heat transfer between the heater and the porous member, wherein the porous member cap includes a side wall 106 for engaging the porous member at points along at least two surfaces, the porous member cap also including at least one fin 110 and at least one channel 112 disposed at an interface with the porous member, and further wherein a pre-load on the porous member cap and the porous member is greater than zero.

13. The method of claim 12, wherein the liquid formulation comprises a solvent with a boiling point of at least 215° C.

14. method of claim 12, wherein the liquid formulation comprises less than about 20% of a solvent having a boiling point less than 215° C.

15. A portable apparatus for dispersing a liquid formulation as a vapor, comprising:

a. a base assembly comprising a porous member cap, a porous member and a housing, wherein the porous member cap includes a side wall 106 for engaging the porous member at points along at least two surfaces, the porous member cap including at least one fin 110 and at least one channel 112 disposed at an interface with the porous member; and b. a head assembly for removably mounting to the base assembly, the head assembly further comprising a heater;

wherein the heater is removably situated in heat exchanging communication with the porous member upon mounting of the base assembly to the head assembly;

wherein the head assembly, when mounted to the base assembly, is capable of providing heat to the porous member for vaporization of the liquid formulation at the interface between the porous member cap and the porous member for release of resulting vapor at an orifice in the heater; and further wherein a pre-load on the porous member cap and the porous member is greater than zero.

16. The portable apparatus of claim 15, further comprising a fitting for removably mounting the base assembly to the head assembly;

wherein the base assembly further comprises a reservoir containing a liquid to be vaporized; wherein an orifice within the porous member cap is in vapor release communication with the orifice in the heater; and wherein the heater is capable of electrical communication with a source of electrical power.

17. A method for the reduction of oozing of liquid from a device for the vaporization of liquid that includes a heat trace containing an orifice having a surface energy, comprising modifying the surface of the heat trace such that the surface energy is less than about 30 dynes/cm, preferably less than about 25 dynes/cm and more preferably less than about 20 dynes/cm wherein the device requires less than 200 Joules of energy per milligram of liquid vaporized, preferably less than 190 Joules of energy per milligram of liquid vaporized, more preferably less than 180 Joules of energy per milligram of liquid vaporized and most preferably less than 170 Joules of energy per milligram of liquid vaporized;

wherein the device comprise a heater, a porous member cap and a porous member matingly configured for heat transfer between the heater and the porous member, wherein the porous member cap includes a side wall 106 for engaging the porous member at points along at least two surfaces, the porous member cap also including at least one fin 110 and at least one channel 112 disposed at an interface with the porous member, and further wherein a pre-load on the porous member cap and the porous member is greater than zero.

18. The method of claim 17, wherein the modifying the surface of the heat trace comprises using, applying, coating or incorporating a treatment medium with at least one of a heat trace and a vaporizer component situated immediately adjacent to the heat trace, and wherein the treatment medium comprises a perfluorinated compound that is heat stable to at least 350° C. and further wherein the vaporizer component situated immediately adjacent to the heat trace is at least one of a porous member cap, a heater substrate and a porous member.

19. The method of claim 18, wherein the perfluorinated compound may be selected from among: polytetrafluoroethylene; fluorinated ethylene propylene copolymer; perfluoro alkoxyalkane copolymer; and ethylene tetrafluoroethylene copolymer; as well as combinations of any of the foregoing.

20. The method of claim 17, wherein the modifying of a heat trace preferably involves the orifice and the closest 10% of the area of the heat trace that surrounds the orifice, more preferably the closest 50% of the area of the heat trace that surrounds the orifice, and most preferably the closest 90% of the area of the heat trace that surrounds the orifice.

* * * * *